United States Patent [19]

Caro

[11] Patent Number: 5,348,002
[45] Date of Patent: Sep. 20, 1994

[54] METHOD AND APPARATUS FOR MATERIAL ANALYSIS

[75] Inventor: Richard G. Caro, San Francisco County, Calif.

[73] Assignee: Sirraya, Inc., San Francisco, Calif.

[21] Appl. No.: 872,926

[22] Filed: Apr. 23, 1992

[51] Int. Cl.$^5$ .............................................. A61B 5/00
[52] U.S. Cl. .................... 128/633; 128/664; 128/665; 356/39; 356/41
[58] Field of Search ............................ 128/633–635, 128/653.1, 653.4, 654, 664–667, 637; 356/39–41

[56] References Cited

U.S. PATENT DOCUMENTS

| | | |
|---|---|---|
| 3,948,345 | 4/1976 | Rosencwaig . |
| 4,223,680 | 9/1980 | Jobsis . |
| 4,281,645 | 8/1981 | Jobsis . |
| 4,303,343 | 12/1981 | Patel et al. . |
| 4,621,643 | 11/1986 | New, Jr. et al. . |
| 4,655,225 | 4/1987 | Dahne et al. . |
| 4,975,581 | 12/1990 | Robinson et al. . |
| 5,012,809 | 5/1991 | Shulze ....................... 128/665 X |
| 5,028,787 | 7/1991 | Rosenthal et al. . |
| 5,054,487 | 10/1991 | Clarke . |
| 5,077,476 | 12/1991 | Rosenthal . |

FOREIGN PATENT DOCUMENTS

0160768A1  11/1985  European Pat. Off. .

OTHER PUBLICATIONS

Jacques, SPIE, 1065:100–108 (1989). Title: Simple theory, measurements, and rules of thumb for dosimetry during photodynamic therapy.

Jobis et al., Neurol. Res., 10:7–17 (1988). Title: Near-infrared monitoring of cerebral oxygen sufficiency.

Mark, H., Anal. Chim. Act., 223:75–93 (1989). Title: Chemometrics in Near-infrared Spectroscopy.

Rockley, M. G., et al., Science, 210:918–920 (Nov. 21, 1980). Title: Fourier-Transformed Infrared Photoacoustic Spectroscopy of Biological Materials.

Wilson et al., Photon Migration in Tissues, ed. B. Chance, Plenum Press, New York, 25–42. Title: Tissue Optical Properties in Relation to Light Propagation Models and In Vivo Dosimetry.

Haaland et al., Analytical Chemistry, LX:1193–1202 (1988). Title: Partial Least–Squares Methods for Spectral Analysis. 1. Relation to Other Quantitative Calibration Methods and the Extraction of Qualitative Information.

Haaland et al., Analytical Chemistry, LX:1202–1208 (1988). Title: Partial Least–Squares Methods for Spectral Analysis. 2. Application to Simulated and Glass Spectral Data.

Primary Examiner—Angela D. Sykes
Attorney, Agent, or Firm—Flehr, Hohbach, Test Albritton & Herbert

[57] ABSTRACT

Disclosed is a method and apparatus for determining the presence and/or concentration of chemical species which absorb electromagnetic energy, dependent to a degree upon the chemical species and the wavelength of electromagnetic energy applied to matter including said species. The absorbed electromagnetic energy generates acoustic energy which is detected and analyzed to determine the presence and/or concentration of the chemical species in the matter.

31 Claims, 13 Drawing Sheets

METHOD AND APPARATUS FOR MATERIAL ANALYSIS

BACKGROUND OF THE INVENTION

1. Field of the Invention

This invention relates to methods and apparatus for the non-invasive quantitative determination of the presence or concentration of chemical species in a multi-component material.

2. Description of the Related Art

Analysis of samples and determination of the concentration of components contained therein is a common and important process in chemistry and biology. Of particular importance is the analysis of biological fluids such as blood, urine or saliva to determine the concentrations of various components. Also of great importance is the measurement of the concentration of various chemical species embedded within a biological material.

The chemical analysis of blood, urine and other biological fluids is crucial to the diagnosis, management, treatment and cure of a wide variety of diseases including diabetes, kidney disease and heart disease. In the case of diabetes, monitoring of blood glucose levels several times per day is a necessary feature of management of the disease for many patients. In the case of people with diseases of the circulatory system, the analysis of various blood components is of importance both in diagnosis and in treatment. For example, the level of cholesterol compounds of various types in the blood of man has a strong correlation with the probability of onset of atherosclerosis. In patients with renal insufficiencies, urine analysis provides valuable information relating to kidney function. In a related application, the concentration of alcohol in blood is known to be correlated to an individual's physical response times and can provide information relating to, for example, the individuals fitness to drive a motorized vehicle.

At present analysis of biological fluid for these and other applications is commonly invasively performed, that is by removing a sample of fluid, and subjecting it to one or more chemical tests. Typically, separate tests are required for each analyte to be measured. These tests require the use of consumable supplies and reagents and are moderately expensive. Often skilled technicians are needed to remove the fluid, and to perform the chemical tests. Frequently the tests are made in centralized clinical laboratories with resulting complexity of sample tracking, and quality control. In such circumstances there are additional problems relating to the potential change in the chemical composition of the fluid between its extraction and its analysis. Furthermore the turnaround time for such measurements can be undesirably long.

Recently there have been developed a number of moderate cost devices for the measurement of analytes using portable monitors. These devices require a drop of the fluid to be analyzed to be placed on a chemically treated substrate. This substrate is then examined by the monitor and a measurement of an analyte is produced. Typical of such devices is the family of devices for self-monitoring of blood glucose concentration such as are marketed by numerous companies in the field of diabetes management. For the limited selection of analytes for which such devices are available they offer the advantage of providing analysis in a short period of time at the patient location. Furthermore, their use eliminates the requirement for the involvement of skilled technical personnel. Although these devices have acceptable accuracy they suffer from the following limitations.

In the case of blood analysis they still require removal of blood, albeit in "finger-prick" quantities. In the case of diabetic management, the removal of blood several times daily presents associated compliance problems, particularly in children, as well as problems relating to the associated physical discomfort and potential for infection. In addition these devices are not readily compatible with continuous blood glucose monitoring such as will be required for improved diabetic management in conjunction with insulin pumps or an artificial pancreas. Furthermore these devices typically measure single analytes only, or in rare instances measure a restricted set of multiple analytes using complex and more expensive chemical or fluid management techniques.

For many applications it would be desirable to be able to make real-time measurements of analytes in biological fluids. Ideally these measurements would be made non-invasively.

An as yet unrealized goal for in-vivo monitoring of biological fluids would therefore be the development of methods and apparatus for the non-invasive, real-time measurement of analytes in a cost effective manner. For in-vitro fluid analysis the ability to make rapid measurements of single or multiple analytes could decrease analysis times, thus boosting the throughput of the clinical laboratories and reducing the cost of the analyses.

In addition to the above applications, there are a number of instances in which it is desirable to measure the local concentration of chemical species in tissue either in-vivo or in-vitro. Specific examples include the monitoring of metabolic function by measurement of tissue oxygenation as described by Jobsis (Neurol. Res. 10, 7–17, 1988), or the measurement of localized changes in tissue blood perfusion such as may be indicative of hyperplastic or neoplastic tissue. Furthermore, it is widely believed that the ability to monitor certain changes in tissue chemical composition may lead to predictive tests for various types of cancer. Examples of such changes are the development of microcalcifications, specific changes in tissue chromophore types and concentrations, and specific variation in tissue hormone levels. Consequently non-invasive methods and apparatus which enabled measurements to be made of the chemical composition of tissue samples in-vivo would also be a very important development.

One approach to non-invasively determining the composition of tissue or of a biological fluid makes use of the interaction of electromagnetic radiation with the matter under examination. It is known that electromagnetic radiation having appropriate characteristics may interact with matter in two primary ways. As it passes through the material the radiation will be scattered and a portion of it will be absorbed. Different chemical species scatter and absorb to different degrees at different wavelengths. The physical composition of the medium will also effect its interaction with the radiation. A number of methods have been proposed that use optical radiation to probe tissue or fluid samples with the goal of determining the concentration of a component of the material by making use of known characteristics of the relationship between optical absorption of the medium and wavelength.

These prior attempts generally share a number of common elements. A source of optical radiation emits light which enters the medium of interest and interacts with the medium, with the result that radiation is both absorbed and scattered by the medium. Subsequently, the attenuated light is detected after it exits the medium, and its intensity as a function of wavelength is measured. The incident light is chosen so that it contains wavelengths that are partially or wholly absorbed by the chemical species for which the concentration is to be measured. Under some conditions it is possible to use the wavelength dependence of the measured intensity of the detected light to determine the absorption coefficient of the medium as a function of wavelength. It is then sometimes possible to use techniques from the fields of chemometrics and statistics to deduce the concentration of individual and multiple analytes within the medium.

Such prior art is represented, for example, by the development of the pulsed oximeter such as is described in U.S. Pat. No. 4,621,643 (New, Jr. et al., 1986). Such a device allows the determination of the percentage of oxygen saturation of the blood (i.e. the relative saturation).

It is also represented by a series of patents, typified by U.S. Pat. No. 4,223,680 (Jobsis, 1980) and U.S. Pat. No. 4,281,645 (Jobsis, 1981), in which similar optical intensity measurements are made in order to quantify relative tissue oxygenation and metabolism using the characteristic optical absorption spectra of both haemoglobin and of the cellular enzyme cytochrome a, $a_3$.

In both of these techniques the presence of high levels of scattering in the tissue prevents the determination of absolute concentrations of these chemical species in the blood or in the tissue. It is possible, however, to obtain relative measurements of their concentrations by making use of specific properties of the absorption spectra of the analytes and taking advantage of the fact that these analytes are present in relatively high concentrations under conditions of clinical significance. Devices based on these principles are now in wide clinical use.

The prior art is also represented by a variety of techniques directed at the non-invasive measurement of blood glucose at concentrations around the normal (fasting) physiological level of 60–115 mg/dl and of numerous other chemical components of blood of physiological significance. Typical of these techniques are those embodied in Rosenthal et al. (U.S. Pat No. 5,028,787), Robinson et al. (U.S. Pat. No. 4,975,581), Barnes et al. (U.S. Pat. No. 5,070,874), Clarke (U.S. Pat. No. 5,054,487) and other related patents.

Unfortunately, in biological samples of practical interest the scattering of the medium is sufficiently strong and wavelength dependent that it is no longer a good approximation to assume that the attenuation of the light in the medium is primarily due to absorption. Nor can scattering be considered as a wavelength independent loss mechanism. For these reasons the techniques described in the prior art result in measurement of an effective attenuation coefficient rather than of an absorption coefficient for the sample. This, combined with the fact that the scattering properties of tissue vary considerably from sample to sample, preclude the use of these prior art techniques for the accurate determination of the concentrations of analytes such as blood glucose at the relatively low concentrations typically of clinical interest.

The key problem in the use of non-invasive techniques such as those above to determine the composition of tissue or of a biological fluid is that the high degree of scattering present in the sample and its intersample variability preclude the development of an accurate algorithm relating the effective attenuation coefficient in the sample to the actual absorption coefficient in the sample. Under conditions where such an algorithm can be developed, techniques developed in the field of chemometrics and statistics have been used in many instances to enable the determination of absolute concentrations of analytes in complex media.

Such techniques have been widely used for the analysis of food and agricultural products. Typically, these techniques rely on careful sample preparation to ensure that there is negligible intersample variation in scattering properties, and then make use of empirical calibration techniques to develop a robust algorithm relating attenuation of incident radiation to absorption and thus ultimately to component concentration. In the case of biological samples such careful sample preparation is not feasible. Furthermore, typical component concentrations measured by such techniques have been in the range of 1% to 50%. The concentrations of interest for biological monitoring are often orders of magnitude smaller with the result that inaccuracies introduced to the measurement as a result of scattering are greatly magnified.

It thus appears that the high scattering, low concentrations and intersample variability inherent in the application of these techniques to biological analysis preclude the direct application of the prior art to non-invasive monitoring. It is clear by analogy to the prior art, however, that accurate deduction of the concentration of a variety of species in blood and tissue could be made using statistical and chemometric techniques if only an accurate measurement could be made of the absorption spectrum of the material rather than of its attenuation spectrum.

It has been shown in the prior art that the technique of photo-acoustic spectroscopy can be used to determine the absorption coefficient of certain types of media and that this technique can sometimes be used in the presence of high levels of scattering in the medium. As described by Rosencwaig in U.S. Pat. No. 3,948,345 the photo-acoustic effect is observed when a modulated light beam is incident on a sample and is modulated at low frequencies, usually below one kHz. As a result of the periodic heating of the material by the modulated absorption of light, thermal waves are generated in the medium, usually a solid. These thermal waves cause thermal fluctuations in a surrounding medium, usually a gas, with the result that a periodic acoustic wave, with a frequency equal to that of the light modulation, is launched into that surrounding medium. This "photoacoustic" wave can be detected, for example by means of a microphone positioned within the surrounding medium. The magnitude of the acoustic signal is determined by the degree of absorption of the radiation in the sample.

Recently this technique has been applied to the analysis of solid samples of biological material by M. G. Rockley et al (Science, 210, 21 Nov., 1980, pp 918–920). This technique of conventional photoacoustic spectroscopy requires the use of a sealed sample cell in which pressure fluctuations can be detected and measured in the gas above the sample. This type of geometry clearly precludes the use of this technique in an in-vivo situation.

In an extension of the conventional photoacoustic technique, Patel and Tam have described a specialized branch of photoacoustic spectroscopy in U.S. Pat. No. 4,303,343. This technique is quite distinct from earlier photoacoustic spectroscopic applications in that the detected acoustic wave is generated in the sample itself rather than in the surrounding medium subsequent to sample heating. In this technique a short pulse of light is incident on the sample with a pulse length that is typically of the order of 1 $\mu$s but may range from $10^{-7}$ to $10^{-4}$ seconds in length. The short and intense light pulse generates a rapid heating of the sample with the resultant generation of an acoustic wave of high frequency in the sample medium itself. This acoustic wave can be detected by means of a fast acoustic detector placed in contact with the medium. Important prerequisites for the application of the technique of Patel and Tam are that the sample be relatively transparent (with an absorption coefficient of less than $10^{-2}$ cm$^{-1}$); that scattering in the sample not be sufficiently great to significantly perturb the intensity distribution of the optical pulse as it travels through the sample; and that the optical beam diameter be small compared with the distance travelled in the medium by an acoustic wave during the optical pulse. Unfortunately, for biological materials of diagnostic interest, the first two of these prerequisites are generally not satisfied while the third is incompatible with measurement geometries of practical utility.

Nonetheless, it remains an important goal for the treatment of a variety of diseases, in particular of diabetes, to be able to measure the concentration of various chemical species within biological fluids or within tissue non-invasively and in real time.

It is, accordingly, the object of the present invention to provide a new and improved method and apparatus using electromagnetic radiation for the detection and quantification of various chemical species within biological media.

A specific object of the invention is to provide a new and improved method and apparatus for measuring the concentration in humans and animals of chemical species such as glucose, cholesterol, alcohol, bilirubin, ketones, fatty acids, lipoproteins, urea, albumin, creatinine, white blood cells, red blood cells, haemoglobin, blood oxygen, inorganic molecules such as phosphorous or various drugs and pharmaceutical compounds in blood, urine, saliva or other body fluids.

A further object of the invention is to provide a new and improved method and apparatus for making such measurements non-invasively, quickly, easily and at reasonable cost.

A further object of the invention is to provide a new and improved method and apparatus for measuring the concentration in tissue of chemical species such as oxygenated haemoglobin, cytochrome a, a$_3$, insulin, glucose, bilirubin, various proteins and chromophores, microcalcifications, various hormones or drugs such as hematoporphyrin derivative (Photophrin).

A further object of the invention is to provide a new and improved method and apparatus for making such measurements non-invasively, quickly, easily and at reasonable cost.

A further object of the invention is to provide a new and improved method and apparatus for measuring the concentration of a variety of chemical components in a complex mixture of fluid media simultaneously, or consecutively within a short time duration.

SUMMARY OF THE INVENTION

Apparatus and methods for determining the composition of a multi-component mixture are disclosed. The method generally comprising the steps of exciting a volume of the multi-component mixture with electromagnetic energy to cause a finite volume of the mixture to generate acoustic energy whose amplitude is dependent upon the wavelength of the electromagnetic energy and the absorption coefficient of the mixture at the wavelength; detecting the generated acoustic energy to generate a representation signal; and correlating the representation signal with the wavelength of electromagnetic radiation and the absorption coefficient to provide an output indicative of the composition.

The apparatus for determining the presence of an analyte in a medium or the composition of a medium is disclosed. The apparatus generally comprises means for exciting a volume of the medium with electromagnetic energy so that the medium generates acoustic energy whose amplitude is dependent upon the wavelength of the electromagnetic energy and the absorption coefficient of the analyte; means for detecting the generated acoustic energy and generating a representation signal in response to the detection; and correlating the signal with the wavelength of electromagnetic energy and the absorption coefficient of the medium to provide an output indicative of the composition.

BRIEF DESCRIPTION OF THE DRAWINGS

The foregoing and other objects of the invention will be understood from the following description when read in conjunction with the accompanying drawings in which.

DETAILED DESCRIPTION OF THE PREFERRED EMBODIMENT

Figure 1:
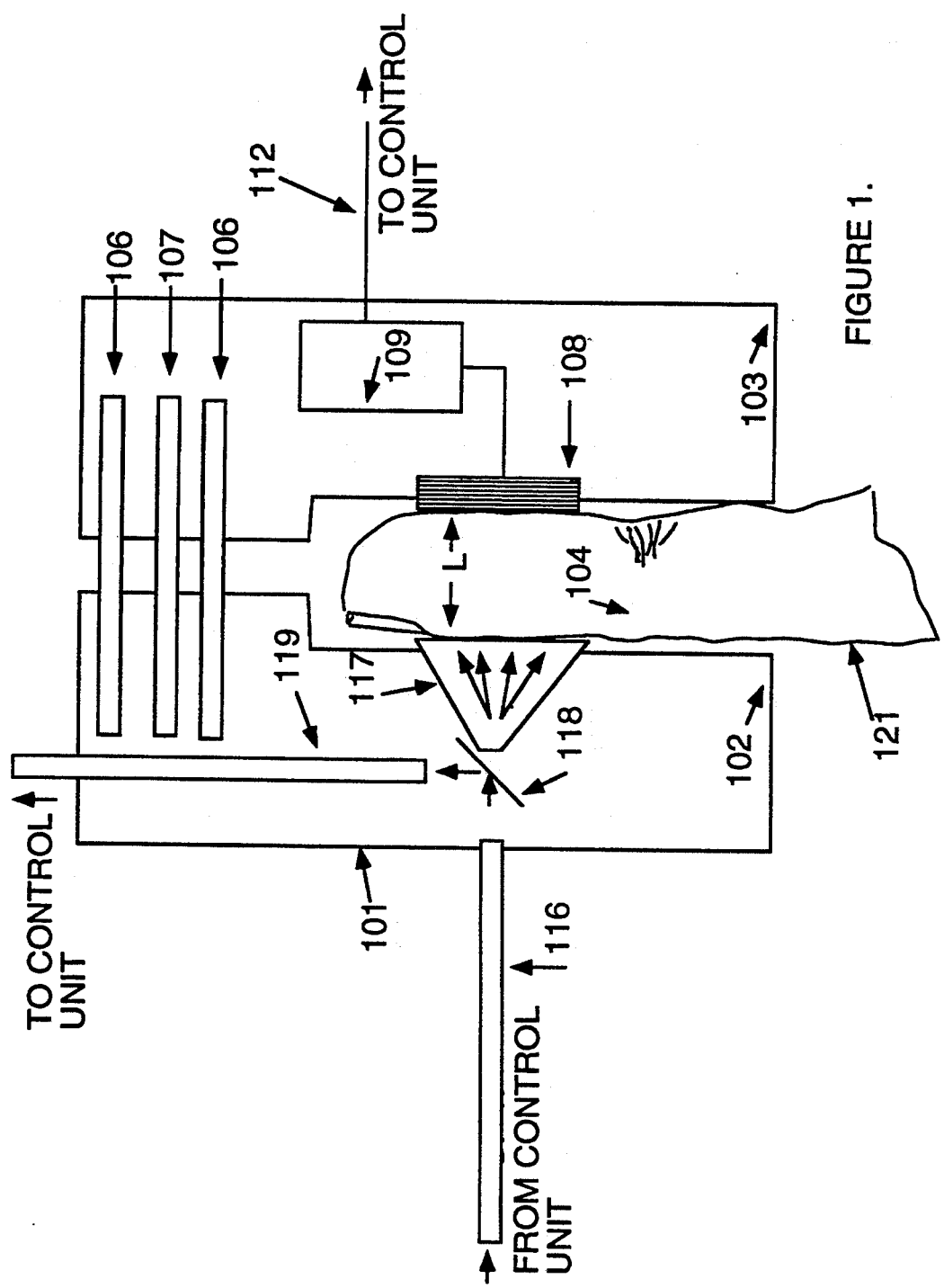
FIG. 1 is an illustration which shows a portion of the apparatus, particularly the clip assembly, associated with a first embodiment of the invention.

This invention involves the absorption of electromagnetic radiation by a material to be analyzed and the consequent generation of an acoustic signal in a manner whereby the acoustic signal provides information useful to determine the composition of the material. The present invention is different from previous photo-acoustic techniques because it is operable in regimes where the prior art cannot be applied. Of particular importance, is that the apparatus and methods of this invention are applicable in situations where the prerequisites of the prior art are violated and are therefore applicable to measurements of in-vivo biological systems. This invention may be practiced with a broad range of electromagnetic spectral frequencies or their wavelength equivalents.

The apparatus and methods according to the present invention allow an acoustic signal, generated in a material as a result of the interaction of electromagnetic radiation with the material, to be used to determine the concentration of components within the material, either alone or in combination with accompanying electromagnetic measurements. The electromagnetic radiation typically has a frequency in the optical range but may also have longer or shorter wavelengths. Such an example would be a pulsed beam of microwave radiation which would interact with tissue and be absorbed, with the resultant generation of an acoustic wave within the medium. Electromagnetic radiation which is multi-spectral in character is used advantageously in the context of the present invention. Such multi-spectral radiation may form either a continuous spectral band, or be spectrally discontinuous, and the spectral components may be present substantially simultaneously or present during different temporal periods.

This invention relies on the fact that when a pulsed beam of electromagnetic radiation passes through an absorbing medium, energy is absorbed from the beam resulting in a pulsatile heating of the medium with a resulting expansion of the region through which the beam has passed. The expansion is accompanied by the generation of an acoustic wave in the medium. The magnitude of the generated acoustic wave is directly related to the amount of energy absorbed in the medium from the beam. Thus, recording the magnitude of the acoustic signal as a function of wavelength provides a direct measure of the amount of absorption in the medium as a function of wavelength.

Once the absorption coefficient of the medium has been determined as a function of wavelength a variety of univariate and multivariate analysis techniques can be used to deduce the individual concentrations of components in the media. This process is conceptually similar to that used in the analysis of food and agricultural products reviewed by Williams and Norris and makes use of a variety of chemometrical and statistical techniques such as the use of discriminant algorithms, multiple regression algorithms, the use of principal component analysis and the use of partial least squares analysis. In general terms a data set, or model, is built up involving known absorption spectra of the various components of interest as well as absorption spectra of a variety of complex samples of partially known composition representative of the range of potential compositions of the sample to be measured. The absorption spectrum obtained from the sample under examination is then compared by the computer with the model data set using analysis techniques such as those described above.

Since the acoustic measurement technique described in this invention is capable of providing accurate measurements of the absorption spectra of media even in the presence of the intense scattering of electromagnetic radiation typical of biological samples, this technique is not subject to the errors involved when similar analysis is performed on spectra of light attenuation such as are obtained using spectroscopic techniques described in the prior art. As a result, these analysis techniques can be used in this invention to accurately determine the concentration of chemical species such as blood glucose present in the sample at low concentration.

The invention is useful for analyzing the composition of a material generally but finds particular utility with respect to biological systems or materials because the apparatus and method are non-invasive and do not subject the material to any apparent damage during the analysis. When the term medium or material is used, such use includes biological tissues or fluid either in-vivo or in-vitro, as well as other materials. Furthermore, the use of the term "tissue" refers in an exemplary fashion to a biological material; however, it should be understood that unless otherwise stated, the method or apparatus so described is not limited to biological tissues.

In FIG. 1 there is illustrated a first embodiment of an apparatus for practicing the present invention. The apparatus includes means for applying electromagnetic radiation to tissue under analysis and a transducer for detecting acoustic energy. The apparatus may include a clip 101, having opposing members 102, 103. The clip can be removably attached to a sample of tissue such as finger 104, Spring means 106 forces the members 102, 103 against the tissue 104. The form of the clip may be altered and shaped for different attachment sites. The spring means 106 may be a flat or coil spring. The members may be urged toward one another by deformed plastic, resilient foams, rubber disks or bands. Hinges and/or pivots may also be used advantageously to achieve the desired application or attachment force, and in such cases the placement of the spring 106 will be such as to take advantage of the leverage. Alternatively, the members 102, 103 may be secured to the tissue by suitable adhesive.

When the apparatus and method of the invention are applied to a determination of the composition of blood, and there is a choice in site selection, the site is optimally chosen so that the appendage is relatively thin and is well vascularized so that there is a considerable volume of blood contained within the tissue. For example, the tissue may be a body appendage such as the ear lobe, nose, or skin fold. A potentiometer 107, or other means for sensing the separation of the clip members 102, 103 of the clip assembly 101, is provided to monitor the tissue thickness, L, and may be contained within the clip assembly 101. A means for sensing an acoustic signal, such as a transducer 108, responsive to the range of acoustic energy signals generated by the operation of the device is attached to one side of the clip assembly 101 in such a way as to make a physical connection between the surface of the transducer 108, and the surface of tissue 104. Preferably in practice, the transducer is covered with an impedance matching substance to approximately match the acoustic impedance of the tissue 104 and the transducer 108. Such matching material may typically be a liquid or gel, and is used to minimize any reflection of the acoustic signal at the interface as may generally occur for materials having dissimilar acoustic impedance characteristics.

The transducer 108, may be of any conventional type and construction. Transducers such as a piezoelectric transducer made of a material such as lead metaniobate, lead zirconate titanate (PZT), or polyvinylidene fluoride (PVDF or PVF2), may be used for example. The transducer should generally have a resonant frequency in the range of 10 kHz to 50 MHz, typically of the order of 1 MHz in this embodiment. Transducers such as the model A125SRM made by Panometrics may be used, for example. Selection of a transducer having resonant frequency characteristics maximizes the sensitivity of detection.

The transducer 108 generates an electrical signal in response to an applied acoustic pressure. As will be described in greater detail below, the acoustic signal is the result of the interaction between an electromagnetic beam and the material being analyzed, specifically the absorption of electromagnetic energy and the consequential localized heating and expansion of the material. The transducer 108 is electrically connected to a low-noise preamplifier 109 which is in turn electrically connected by a cable 112 to control unit 111, FIG. 2, which includes radio-frequency (rf) and digital circuitry 113, and computer 114.

Figure 2:
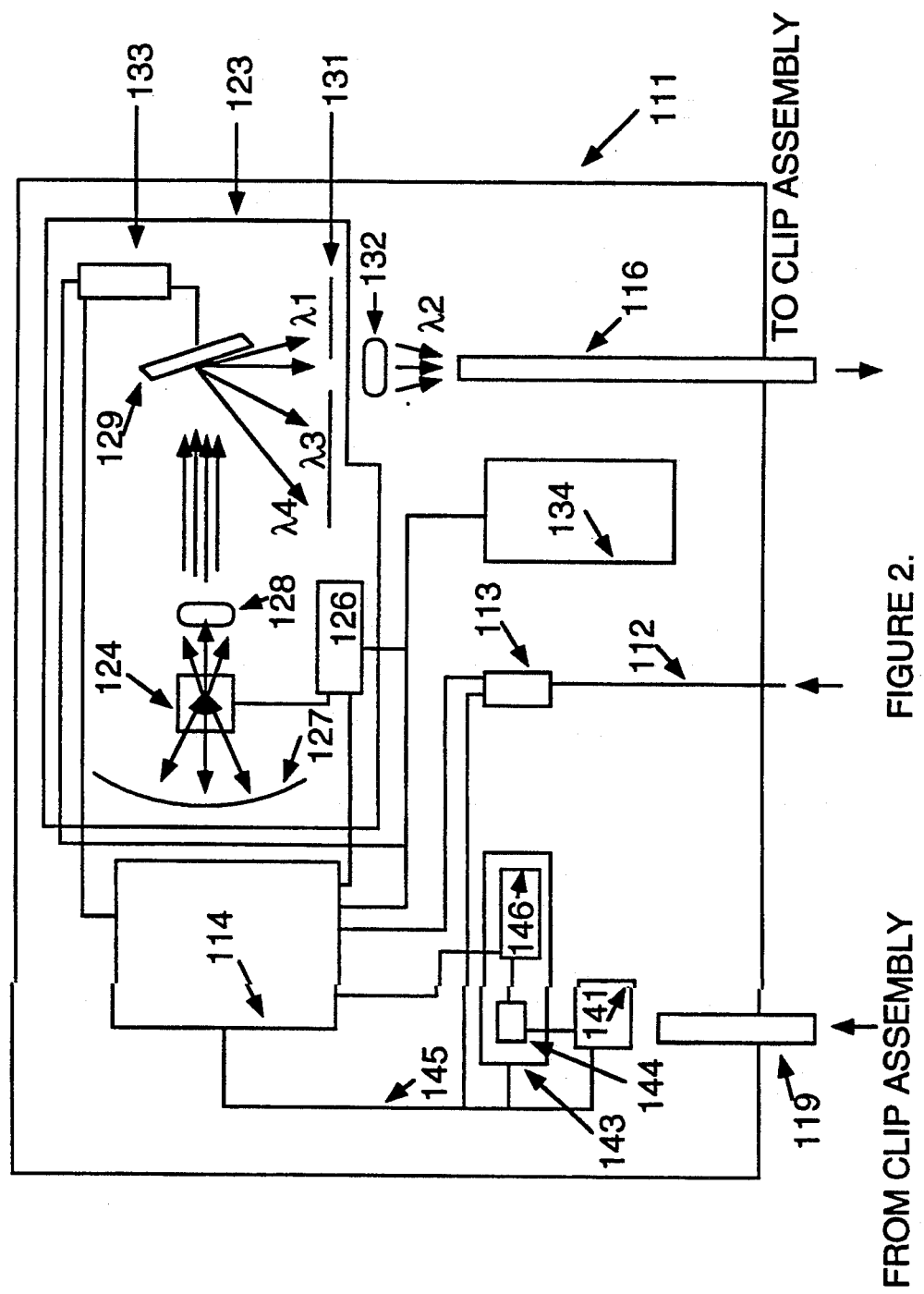
FIG. 2 is an illustration which shows a portion of the apparatus, particularly the control unit, associated with a first embodiment of the invention.

Substantially opposite to transducer 108 is fiber optic means 116 which may comprise a single fiber of suitable size that delivers electromagnetic radiation in the form of light from the control unit 111, FIG. 2, to the tissue 104. Under some circumstances the beam from fiber optic means 116 may be altered, such as by expanding the beam by beam expansion means 117, such as a lens system, tapered fibers, or other conventional optical or electromagnetic beam shaping devices, so as to illuminate the tissue sample over an area different than would be achievable from the unaltered output of fiber optic means 116.

When electromagnetic radiation other than light is used, methods and apparatus analogous to fiber optics may be used to irradiate the tissue 104. For example for an apparatus employing microwave radiation, a coaxial cable may be used for frequencies below 1 GHz while at higher frequencies a waveguide may be used.

A portion of the electromagnetic energy emanating from optical fiber means 116 is split off by a beamsplitter 118 and collected by a second optical fiber means 119. The second optical fiber means 119 is also connected to the control unit 111, FIG. 2. For a given wavelength, the light intensity measured at the control unit 111 from optical fiber 119, is linearly related by a constant multiplicative value to the light intensity entering the tissue through surface 121. The multiplicative constant is known generally from the design of the apparatus, and may be determined more precisely from a calibration procedure.

In FIG. 2 there is illustrated a control unit 111, which comprises several components. It may be desirable to include substantially all of the components into a single unit, possibly even incorporating some or all the electronics into the body of clip assembly 101.

The control unit 111 illustrated in FIG. 2 contains a source assembly 123 of tunable radiation. In this embodiment the radiation is in the optical wavelength range, such as between 400 and 3000 nm, and more particularly between 600 and 2500 nm. The source assembly 123 includes an intense light source 124 such as a xenon arc-imp, for example, Hamamatsu model L2274 or L2189 or a tungsten lamp, for example, Hamamatsu model L2192. The light source is driven by a source power supply 126 which is pulsed to produce optical pulses with a duration of approximately 1 $\mu s$ ($10^{-6}$ seconds). In other embodiments this optical pulse duration may be in the range from $10^{-9}$ to $10^{-3}$ seconds. The pulsed light source may consist of a pulsed lamp, or it may consist of a continuous light source followed in the optical system by a mechanical chopper wheel, shutter, or acousto-optic or electro-optic modulation device (not shown) for convening a continuous beam of light into a pulsed beam.

The light from the light source 124 is refocused by concave reflector 127 then collimated by a source lens 128. The geometry of the light source 124, concave reflector 127, and source lens 128, direct the radiation so that it is incident on a grating 129. Concave reflector 127 may have a spectrally selective reflective coating such that any undesirable spectral components, such as thermal infrared spectral components (3000 to 20,000 nm), are not reflected into the source lens 128. Other spectral filters such as heat absorbing glass (not shown) may be similarly interposed in the optical system.

Light which is incident on grating 129, is diffracted into a continuous spectra of component wavelengths. For example, $\lambda_1$, $\lambda_2$, $\lambda_3$, and $\lambda_n$, are components of a beam containing a plurality of wavelength components which are differentially diffracted from a multi-spectral beam causing them to be spatially displaced from one another by the grating 129. Electromagnetic radiation (light in this case) of a specific wavelength is selected by aperture 131, which may have the form of a narrow slit, passes through lens 132 and is focused into optical fiber means 116. Because the grating 129 spatially disperses the electromagnetic radiation, the grating control system 133 operates in conjunction with the aperture 131 so that the selected wavelength band passes through the aperture 131 and enters the optical fiber means 116. This may be accomplished by mechanically translating the grating 129, by rotaing the grating 129 through the appropriate angle, or by translating the aperture 131, lens 132, and optical fiber means 116 together so they intercept the desired portion of the dispersed electromagnetic beam. In other embodiments the grating may be replaced by a holographic grating, an acousto-optic tuneable filter, a set of filter wheels or prisms, or some other means of converting a broad band spectrum into tuneable narrow-band wavelength light. The dispersion characteristics of the grating 129, which determines the separation of the multi-spectral beam into its component wavelengths, and the width of the aperture 131 are determined by the geometry in which components 116, 124, 127, 128, 129, 131 and 132 are arranged, the optical properties of the source and the desired spectral resolution of the absorption spectra. The grating is tuned by means of a grating control system 133. Both the grating control system 133 and the source power supply 126 are controlled by the computer 114 and power to drive all three is provided by a built in power supply 134.

Figure 3:
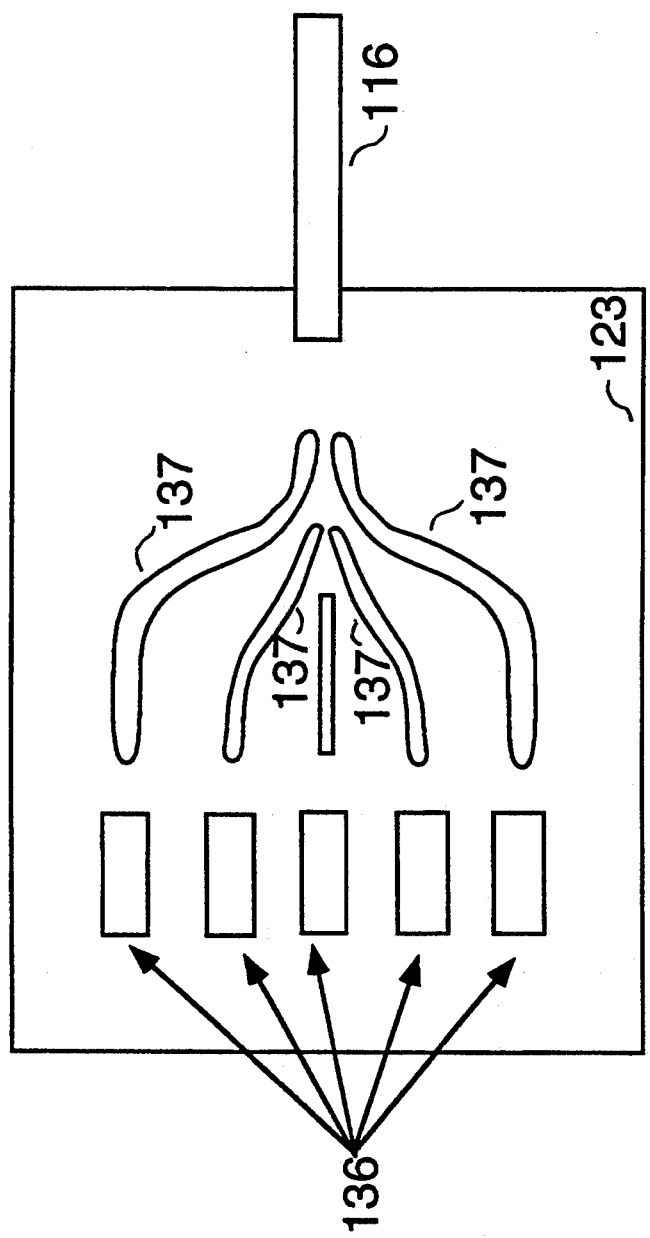
FIG. 3 is an illustration which shows an embodiment of the apparatus according to this invention which employs light emitting diodes.

There are several possible embodiments for the radiation source assembly 123. In an alternative embodiments the tuneable light source 124 is replaced by one or more diode lasers or light emitting diodes 136 as illustrated in FIG. 3. In such an alternative embodiment the diode lasers or LED's 136 are narrow-band emitters and are coupled into the optical fiber means 116 sequentially in time. Multiple fiber means 137 are alternatively used to couple the multiple sources to the optical fiber means 116 or directly to the beamsplitter 118. The lasers or LED's 136 may be selected to be tuneable electronically over the wavelength range of interest.

The radiation source assembly 123 may comprise a Fourier Transform spectrophotometer or Hadamard spectrophotometer with output wavelengths ranging from 500 to 2500 nm. In this case the radiation source provides a wide range of wavelengths simultaneously, which are modulated by the spectrophotometer in such a way as to make reconstruction of the spectrum of the observed signal readily feasible. The interchangeability of dispersive spectrophotometers and Fourier Transform spectrophotometers is widely understood in the art.

Referring again to the embodiment illustrated in FIG. 2, the light is tuneable from about 500 nm to about 2500 nm.

The light incident on the tissue 104 enclosed by the clip assembly 101 is pulsed radiation having a controlled bandwidth and a controlled time varying center wavelength. The bandwidth should be chosen commensurate with the degree of precision needed in the measured absorption spectrum; narrow bandwidth radiation provides greater spectral resolution. The light collected by optical fiber means 119, FIG. 1, is transmitted to the control unit 111 where it is detected by a detector assembly 141 and its intensity is measured. Means for collecting and directing the light from beamsplitter 118 such as a lens may optionally be used to direct the light into the entrance face of optical fiber means 119. The electrical output from detector assembly 141 is amplified and processed by low-noise electronic circuitry 143 which comprises a low noise amplifier 144 and a resetable peak-hold circuit 146. The resulting signal is transmitted to the computer 114. The detector assembly 141 and electronic circuitry 143 may be incorporated into the clip assembly 10 1, and the electrical signal communicated to the computer 114.

Substantially concurrently with the transmission of the processed optical signal to the computer 114, the amplified signal from the acoustic transducer 108, FIG. 1 is transmitted to the control unit 111, FIG. 2, where it is processed electronically by low-noise radio-frequency (rf) and digital circuitry 113 and the resulting signal is sent to computer 114. The signals from the electronic circuitry 143 and radio frequency and digital circuitry 113 are read by the computer between pulses of the light source 124. Alternatively, the measurements may be stored in an interface buffer or memory store to minimize the processing burden on the computer 114. Control lines run between the computer and the various electronic, electro-mechanical, electro-optical and acousto-optical components to affect synchronism of operation.

Figure 4:
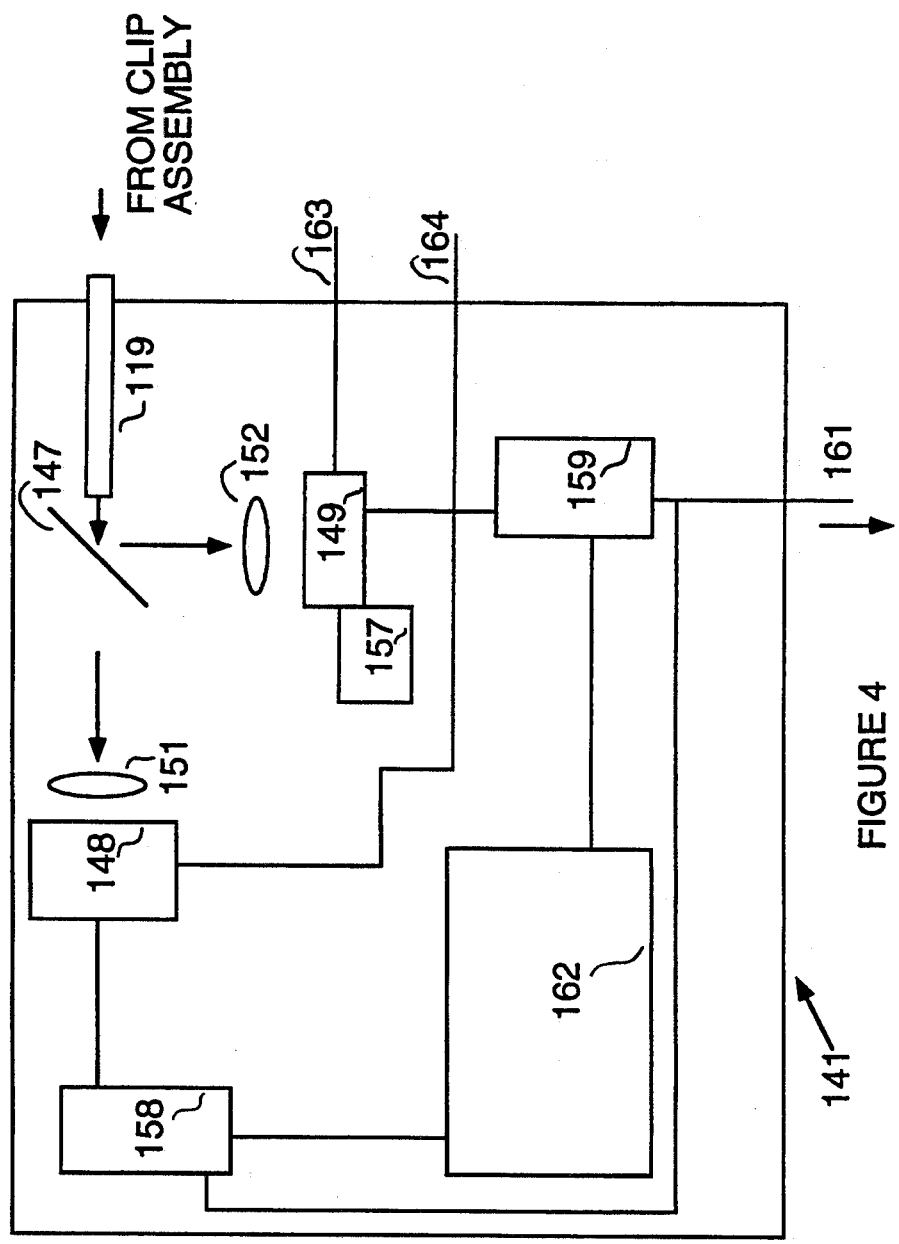
FIG. 4 is an illustration which shows a portion of the apparatus, particularly the detector assembly, associated with a first embodiment of the invention.

Detector assembly 141, FIG. 2, can be of several types. In the embodiment described here detector assembly 141 is actually a package consisting of two detectors as shown in the illustration of FIG. 4. Each detector assembly 141 includes a beam splitter 147 which transmits a portion of the light from fiber optic means 119 onto a silicon photodiode 148. The photodiode is typically a large area avalanche photodiode such as model TL15CA2 manufactured by Advanced Photonix, Inc., or the more common silicon photodiode such as that manufactured by Hamamatsu. The light reflected by the beamsplitter 147 is incident on a lead selenide or lead sulfide detector 149 such as model OTC 12S-8T or OTC-22S-ST detector manufactured by OptoElectronics Textron. These detectors are thermoelectrically cooled by a cooler 157, so as to reduce thermal noise and enhance sensitivity. In some embodiments these detectors might be replaced by photomultipliers for greater sensitivity. The development of detectors having sensitivities extending continuously from visible wavelengths into the near-infrared (approximately 350 nm–2500 nm) will permit the use of a single detector, or detector array without the need to switch detectors.

Lenses 151 and 152 are placed in front of each photo detector 148, 149 to concentrate the incident light beam onto the relevant detector 148, 149 and to match the geometrical characteristics of the incident light to the size and acceptance angle of the photo detector 148, 149. The electrical output from each photo detector 148, 149 is processed by electronic amplifiers 158, 159 and communicated to the processing electronics 143, FIG. 2, via lead 161. A power supply 162 powers the detectors and electronics in the detector assembly 141. For wavelengths shorter than about 850–1100 nm the signals from the silicon photodiode detectors are read by the computer and used for subsequent processing. For longer wavelengths the computer uses the signals from the lead salt detectors. The signals from the other detector in each case is ignored. The detector selection may be effectuated by the computer 114 via the detector control lines 163, 164 or it may be effectuated in subsequent processing of the data.

In operation the clip assembly 101 is clamped to a sample of tissue 104, a patient's finger for example, and firmly held to the finger tissue 104 as a result of the spring loading 106. The light source 124 is switched on and off (pulsed) repetitively, at a frequency of 1–10 kHz in this embodiment, in response to a command from computer 114.

At each consecutive pulse, the wavelength of the light incident on the patient's tissue 104, is shifted or scanned by the wavelength scanning means, in this embodiment the grating control system 133, and the grating 129, controlled by computer 114. The wavelength of the light may be shifted in increments of 10 nm. The wavelength increment is chosen so as to provide the desired spectral resolution of the measurements. In this embodiment the spectrum of wavelengths from 500 nm to 2500 nm is scanned. The entire wavelength spectral range from 500 nm to 2500 nm requires 200 pulses, each pulse having a center wavelength shifted by 10 nm and having a 10 nm spectral bandwidth. The entire wavelength spectral range from 500 nm to 2500 nm, is scanned 50 times per second. The wavelength range is repetitively scanned so that the measurements at each wavelength can be processed to increase the signal to noise ratio, and compensate for variations in the measurements such as patient motion, pulsatile blood flow and effects related to breathing. The total scanning period, or equivalently, the number of times the wavelength range is scanned is selected by the operator and is generally dependent on the characteristics of the material, and the required data resolution, which relates to the signal-to-noise ratio. Operation of the light source and tuning element is controlled by computer 114 within the control unit 111. Control signals are provided between each of the electrical, electro-mechanical, and electro-optical components in FIG. 2. To provide synchronization and proper data transfer among the several components of the apparatus, there are control lines 145 provided between computer 114 and each of electronic circuitry 143, detector assembly 141, radio-frequency and digital circuitry 113, source power supply 126, grating control system 133. Control lines 145 are also provided to an electronic shutter, electro-optical modulator, acousto-optic modulator, or other means to modulate (pulse) the light source 124 in embodiments of the invention employing those devices.

At each radiation pulse, the radiation is transmitted to the clip assembly by optical fiber means 116. The radiation entering the clip assembly 101 is split between the earlobe tissue 104 and the optical fiber means 119. The intensity of the radiation incident on the tissue 104 is directly proportional to the intensity of radiation collected by optical fiber means 119. That radiation is transmitted to detector assembly 141, sensed by detectors 148, 149, and amplified by amplifiers 158, 159. The signals are then converted to a digital form by an analog to digital converter in the interface. Alternatively the signals may be converted into a digital form in the post detection processing electronics and transmitted to the computer 114. The measured data are stored in a storage device, such as electronic memory, a disc drive, magnetic tape, optical disk, or any other form of data storage.

Figure 5:
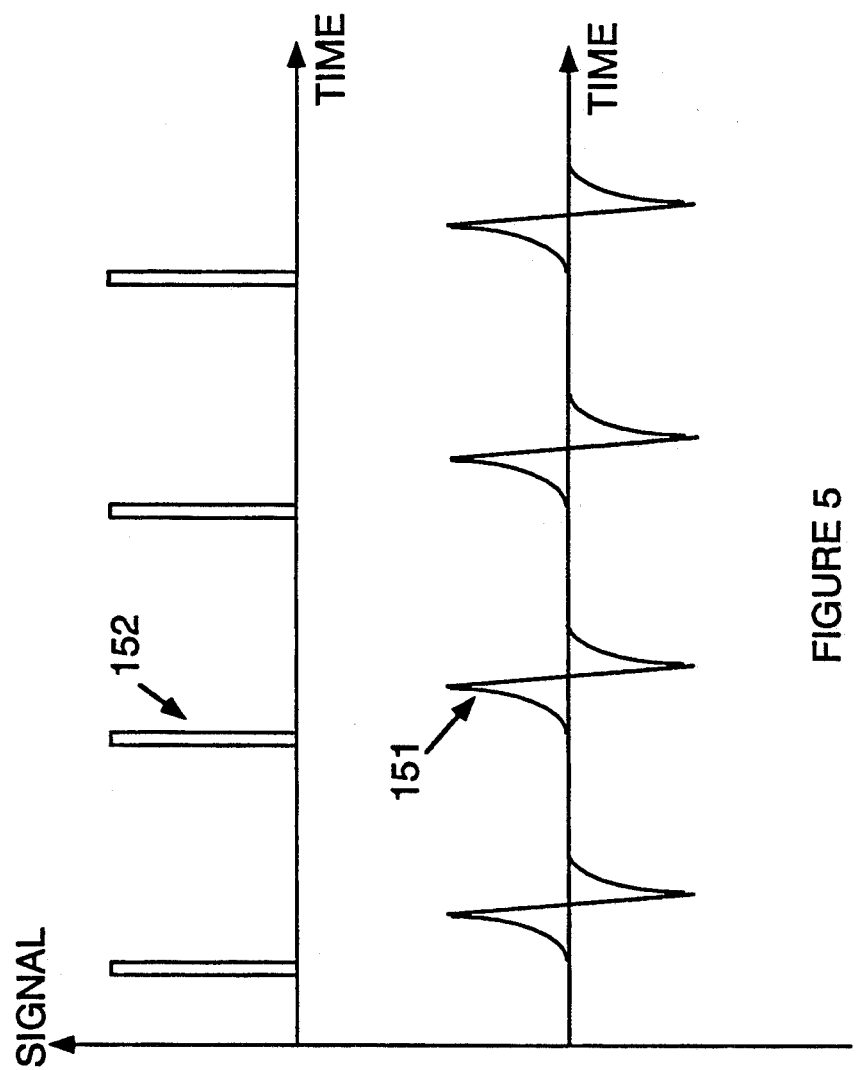
FIG. 5 is an illustration which shows the electromagnetic pulses applied to the material and the resulting acoustic signals.

The intensity of radiation at the surface of the tissue 104 is designated by $I_0(\lambda)$. The actual measurement of the acoustic signal, $P(\lambda)$, occurs as follows. At each radiation pulse, an acoustic signal is generated in the medium as a result of the absorption of energy by the medium and its subsequent expansion. A typical acoustic pulse 151 as generated in the medium 104 responsive to the electromagnetic pulses 152 is illustrated in FIG. 5.

The signal from the transducer 108, in FIG. 1, is passed through low noise amplifier 109, to digital circuitry 113. The signal will generally be a bipolar photoacoustic signal such as that illustrated in FIG. 3 and enlarged in FIG. 6.

An average value of the measured optical signal $I_0(\lambda)$ at each spectral wavelength is determined using signal processing techniques, such as averaging a predetermined number of pulses. Similarly, an average value of the acoustic signal $P(\lambda)$ for each spectral wavelength is determined using signal processing techniques, such as averaging a predetermined number of pulses. Different processing techniques may be employed for the optical signal and the acoustic signal, however, simple signal averaging may suffice in each instance.

In a typical embodiment, signals are collected over elapsed periods of time ranging from approximately 1–10 seconds; the equivalent of 10,000 to 100,000 pulses. The measured signal values at each spectral wavelength are averaged to produce average values of $I_0(\lambda)$ and $P(\lambda)$ as functions of wavelength from 500 to 2500 nm. These averaged values are then processed to determine the absorption coefficient of the medium, and ultimately to correlate the measured absorption characteristics with those of known models and thereby to determine the concentration of specific chemical species within the medium. The method for determining the material absorption coefficient from the processed average values is described below.

Figure 7:
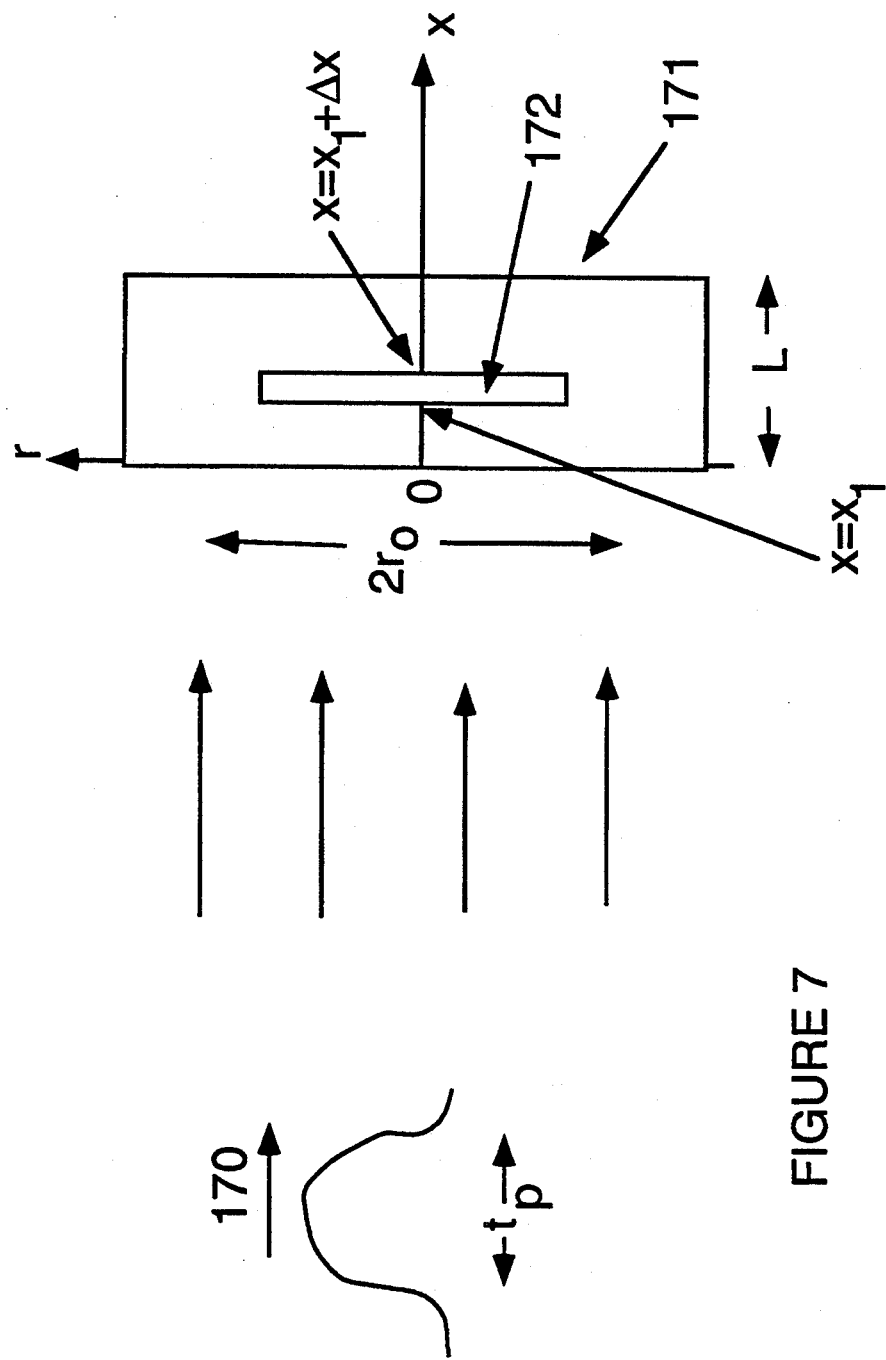
FIG. 7 is an illustration which shows the geometry associated with a beam of electromagnetic radiation incident on a sample of material to be analyzed.

The theory of the photo-acoustic effect has been widely discussed in the literature. We will discuss here only those details necessary to explain the improvements of this invention over the prior art. Consider a pulsed beam 170 of radiation of circular cross section with radius $r=r_o$, incident on the surface of a sample, 171, of material as illustrated in FIG. 7. Let the planar beam enter the medium at normal incidence to its surface and let the intensity of the beam be represented by $I(r,x,t)=[I(r,x)*f(t)]$, where r and x are cylindrical coordinates with the x axis being the direction of propagation of the beam and t the time. Let the incident pulsed beam have a pulse width of $t_p$, a temporal pulse shape $f(t)$, and let the material extend from $x=0$ to $x=L$ along the direction of propagation of the beam and have a semi-infinite extent along the r axis. Let the wavelength of the radiation be tuneable and represented by $\lambda$.

In this invention the radiation pulse width, $t_p$, is chosen to be less than the time corresponding to a thermal diffusion distance of the lesser of the dimensions L and $r_o$. This requires that $t_p < (A^2/4D)$ with A being the lesser of L and $r_o$, and D being the thermal diffusivity of the medium, typically of the order of $10^{-3}$ cm$^2$ sec$^{-1}$. For L=0.5 cm this constraint would imply only that $t_p < 60$ s. Even for small values of $r_o$ such as $r_o = 10^{-2}$ cm, this restriction only limits $t_p < 25$ ms.

As a result of the interaction with the above pulsed radiation, the peak amplitude of the acoustic pressure wave generated by a small volume element of material, 172, in the shape of a rectangle of dimensions R and $\Delta x$ at co-ordinates $(0,x_1)$, as illustrated in FIG. 7, can be described by the expression $$P(\lambda)=[St_p/(\Delta x)]I(o,x_1)*[1-\exp(-\mu_a*\Delta x)] \qquad (1)$$

where S is a constant dependent on properties of the medium given by $S=[v^2\beta/C_v]$, v is the speed of sound in the medium, $\beta$ is the thermal expansion coefficient of the medium, and $C_v$ is the specific heat at constant volume of the medium. $\mu_a$ is the absorption coefficient of the sample at the incident wavelength, $\lambda$, in the volume element, and $r_o > x_1$. In this geometry the generated acoustic wave can be considered as a plane wave propagating along the x axis and $P(\lambda)$ is measured at a point on the x axis. The attenuation of the acoustic wave as it propagates through the medium is ignored for the purposes of this illustrative analysis, but is a well understood phenomenon which can be taken into account if necessary.

As the beam of electromagnetic radiation incident on the medium penetrates into the tissue, its intensity drops rapidly as a result of scattering and absorption in the tissue. The majority of the photo-acoustic signal will therefore come from the initial depth of tissue in which the light intensity is a maximum, although there will be additional smaller contributions from deeper in the tissue. Thus a reasonable approximation for the peak acoustic signal detected, for a given wavelength of incident radiation, is given by Eq. (1) where $\Delta x$ equals d, the penetration depth of the radiation into the tissue. We define the penetration depth, d, as the distance within the tissue along the x axis in which the incident light intensity fails by a factor of exp (−1). In order to use Eq. (1) to deduce the absorption coefficient of the medium $\mu_a(\lambda)$, from the measured values of acoustic pressure, $P(\lambda)$, it is necessary to have an understanding of the values of radiation intensity within the medium and of the value of d.

The analysis of light transport through a scattering medium is complex and has been recently much studied. A useful review of the subject is given by Wilson et al in "Photon Migration in Tissues" ed. B.Chance, Plenum, pp 25–42. The nature of the transport of a broad beam of light through a relatively thin sample of tissue is strongly effected by the values of the absorption coefficient, $\lambda_a$, and the scattering coefficient, $\lambda_s$. In typical tissue samples, the scattering is highly forward-peaked Mie scattering defined by a Henyey-Greenstein function with g=0.94–0.98. The effective scattering transport coefficient for such tissue is given by $\mu'_s=(1-g)\mu_s$. In general, radiation transport can be described by Beer's law for the case that $\mu'_s << \mu_a$, and by diffusion theory for the case that $\mu'_s >> \mu_a$. In the intermediate regime where scattering and absorption are effectively comparable, complex numerical analysis is generally required to describe the radiation transport. As a result, analysis of the acoustic signal generated in this invention can be separated into three regimes differentiated by the relative values of $\mu'_s$ and $\mu_a$.

Regime (a): $\mu'_s >> \mu_a$:

Making use of the analysis of Wilson et al., for the case that $\mu'_s >> \mu_a$, the transport of a broad beam of light through a relatively thin sample of tissue can be described by the formula $$I(0, x) = I(0,0) * k * \exp(-\mu_{eff} * x) \qquad (2)$$

where k is a constant discussed later, and the effective attenuation coefficient is given by $$\mu_{eff} = \{3\mu_a(\mu_a + \mu_s(1-g))\}^{\frac{1}{2}} \qquad (3)$$

It has been shown by Jacques (SPIE Vol 1065, Photodynamic Therapy: Mechanisms, 1989) that the effective penetration depth, d, is given by $$d = 1 + \ln(k))/\mu_{eff} \qquad (4)$$

so long as $\mu'_s >> \mu_a$. The value of k is also discussed by Jacques, and it is shown that typically ln(k) is in the range of 0.5–2 and so d is typically of the order of (1.5–3)/$\mu_{eff}$. For typical tissue at the near infrared wavelengths, $\mu_s=300$ cm$^{-1}$, $\mu_a=0.5$ cm$^{-1}$, g=0.96, and the above Eqs. (3) and (4) imply values of $\mu'_s=12$ cm$^{-1}$, $\mu_{eff}=4$ cm$^{-1}$, and of d=0.4–0.8 cm.

In this regime, taken to be the region where $\mu'_s > 10 \mu_a$ and typically extending over a wavelength range from 600 nm to 1300 nm, the generated photo-acoustic signal for the geometry of embodiment 1 is given from Eq. (1) by $$P(\lambda) = [0.7 * St_p * I(0,0)]\mu_a \qquad (5)$$

where the exponential of Eq. (1) has been expanded in a power series and the higher order terms are ignored since $\mu_a d < 0.5$ in this regime.

Regime (b): $\mu'_s < \mu_a$:

Although Beer's law is generally valid only in the regime $\mu'_s << \mu_a$, we are primarily concerned in this invention with the intensity distribution within the initial penetration depth of the radiation into the tissue. In this limited spatial region the intensity is quite well described by Beer's law for all values of $\mu'_s < \mu_a$. In this regime, typically for wavelengths in the range of 1350 nm to 2500 nm, the radiation transport can be described by $$I(0,x) = I(0,0) * \exp(-\mu_a * x) \qquad (6)$$

In this case, the penetration depth d=$\mu_a$ and the generated photo-acoustic signal in embodiment 1 is given from Eq. (1) by $$\begin{aligned} P(\lambda) &= [0.7 * St_p/d]I(0,0) * [1 - \exp(-\mu_a * d)] \\ &= [0.4 * St_p]I(0,0) * \mu_a \end{aligned} \qquad (7)$$

It can be seen that in both regimes (a) and (b) the detected acoustic signal has a simple dependence on the optical absorption coefficient, $\mu_a$, independent of the scattering parameter, $\mu'_s$. Since S and $t_p$ are known or can be determined from calibration procedures, the measurement of P ($\lambda$) allows the accurate determination of $\mu_a(\lambda)$. It is only in the third regime, where $\mu_a < \mu'_s < 10 \mu_a$, that the relationship between P ($\lambda$) and $\mu_a$ is less simple. This regime is primarily relevant only for wavelengths in the range of 1300 to 1350 nm and below 700 nm. In that regime more complex mathematics should also allow relationships to be developed between P ($\lambda$) and $\mu_a$ if necessary.

The region covered by this formalism covers substantially the range of wavelengths of interest for the applications discussed here, namely 500 nm–2500 nm with small gaps in the range 1300–1350 nm and below 700 nm. Even in those regions this formalism can be extended with some adjustment of the formulae and some loss of accuracy. As a result this invention makes possible the accurate determination of the absorption coefficient of biological media over a broad range of wavelengths and a range of degrees of absorption independent of the level of scattering in the sample. This result stands in stark contrast to conventional techniques of absorption spectroscopy, based on transmittance or reflectance measurements, in which $\mu_{eff}$ is determined from measurement and $\mu_a$ is inferred using correlation techniques which have an accuracy dependent on the level of scattering in the sample.

Once the absorption coefficient of the medium has been determined as a function of wavelength over the wavelength range of interest, it is necessary to correlate the absorption spectrum of the medium with a model data set including known absorption spectra of the various components of interest as well as absorption spectra of a variety of complex samples of partially known composition representative of the range of potential compositions of the sample to be measured. As a result of this correlation, the absolute and relative concentrations of a variety of chemical species within the medium can be accurately determined.

In making this correlation, the computer, 114, employs a variety of algorithms depending on the tissue and component species that are of interest. The correlation techniques and algorithms are typical of those employed in the field of chemometrics and include a variety of univariate and multivariate analysis techniques such as the use of discriminant algorithms, multiple regression algorithms, the use of principal component regression analysis and the use of partial least squares analysis. Such techniques are referenced in Robinson et al. (U.S. Pat. No. 4,975,581) and discussed by Mark (Anal. Chem. Act. 223, 75–93, 1989) as well as by Haaland et al. in Analytical Chemistry, Vol. LX, p. 1193 (1988) and in Analytical Chemistry, Vol. LX, p. 1203 (1988).

Typically these correlation techniques employ absorption data obtained at several separate wavelengths. This multivariate approach has the important advantages of increasing accuracy and precision while at the same time allowing the use of techniques for the detection, recognition and exclusion of "outlier" samples. Such "outlier" samples are those samples that do not exhibit typical correlations between absorption properties and component concentrations. Their identification is important in the development of an accurate calibration model. It is also important to identify situations where the sample to be analysed (the patient, for example), is itself an outlier and to provide notification in the rare cases where such samples can not be correctly analysed as a result.

The model data set used by the computer 114 to deduce component concentrations from measured absorption coefficients can be developed during manufacture of the invention and stored in the memory of the computer at that time. Alternatively, the model data set can be made to be specific to a particular individual, or class of individuals. In that case the invention may include the provision for calibration of its model data set from time to time during use. The invention may include provision for input of user specific model data sets. This input could be in the form of an external memory device that can be attached to the invention, electronic communication with a device that contains said patient specific model data set, or a plug-in module consisting of electronic memory in which said data set is contained.

Figure 8:
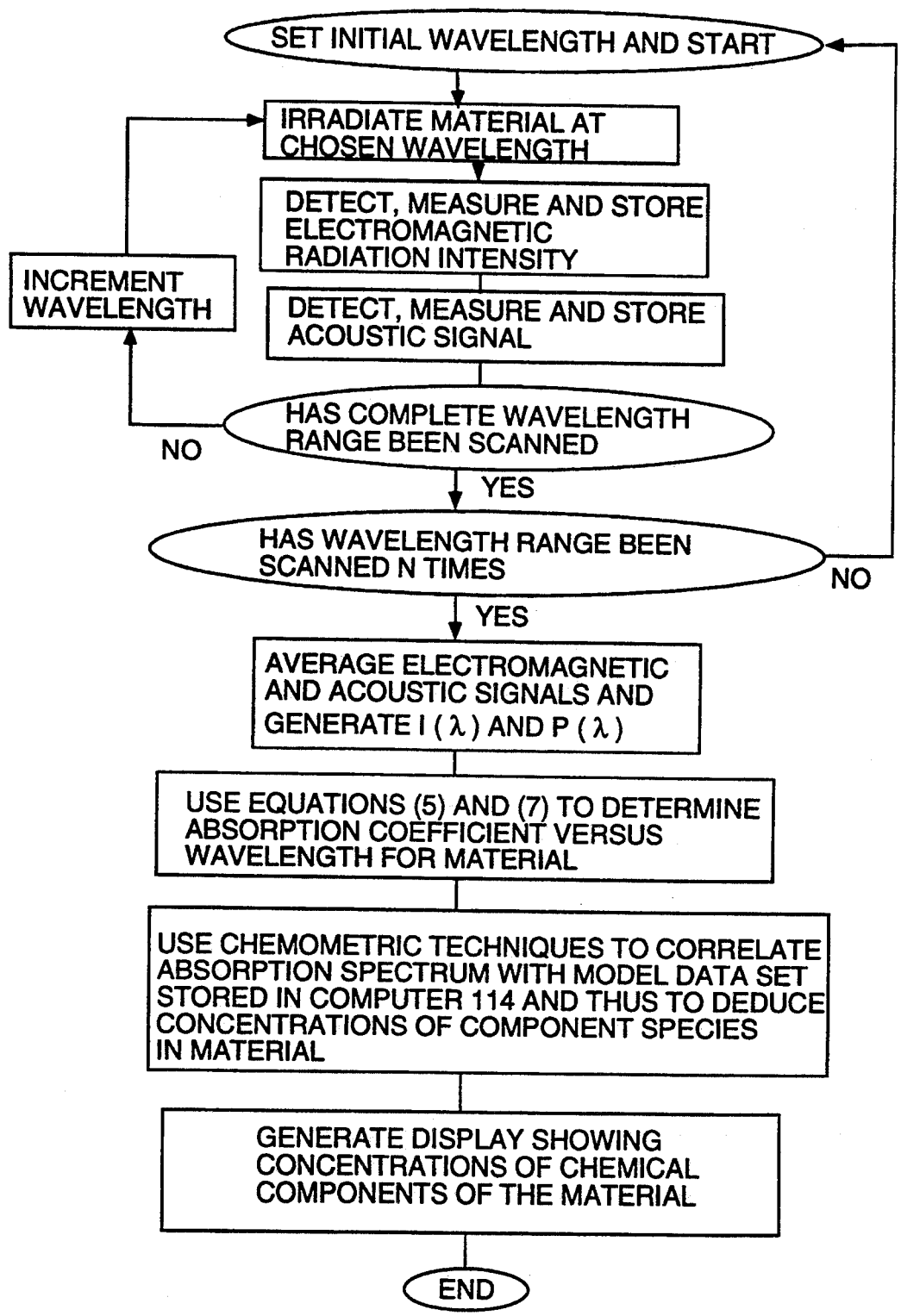
FIG. 8 is an illustration which shows a flow-chart diagram of an embodiment of a method according to the present invention.

The process employed in determining the absorption coefficient $\mu_a(\lambda)$ for a material is shown in the flow chart diagram, FIG. 8.

The first step involves irradiating a medium with pulsed electromagnetic radiation at a first wavelength so that acoustic energy is produced in the medium. The next step involves detecting the irradiating electromagnetic radiation and then measuring and storing the amplitude of the irradiating electromagnetic radiation. The method also comprises the step of detecting the acoustic energy induced by the electromagnetic radiation with a transducer, and measuring and storing a value for the acoustic energy. This includes generating a signal from the transducer in response to the detected acoustic energy; amplifying the signal with a low-noise amplifier; integrating the amplified signal; peak-hold detecting the amplitude and arrival time of the peak of the integrated signal; and storing a value for the peak arrival time. The incident electromagnetic wavelength is then changed by a predetermined amount; repeating these steps for a plurality of electromagnetic energy wavelengths spanning the spectral region of interest; and then repeating all of the above steps a plurality of times; signal averaging each of the measured and stored values for each of the electromagnetic wavelengths; calculating a value for the peak acoustic signal based on the signal averaged measured values; calculating the absorption coefficient for each electromagnetic wavelength; and correlating the calculated absorption coefficient with a plurality of known spectra to determine the presence and concentration of analytes.

Figure 9:
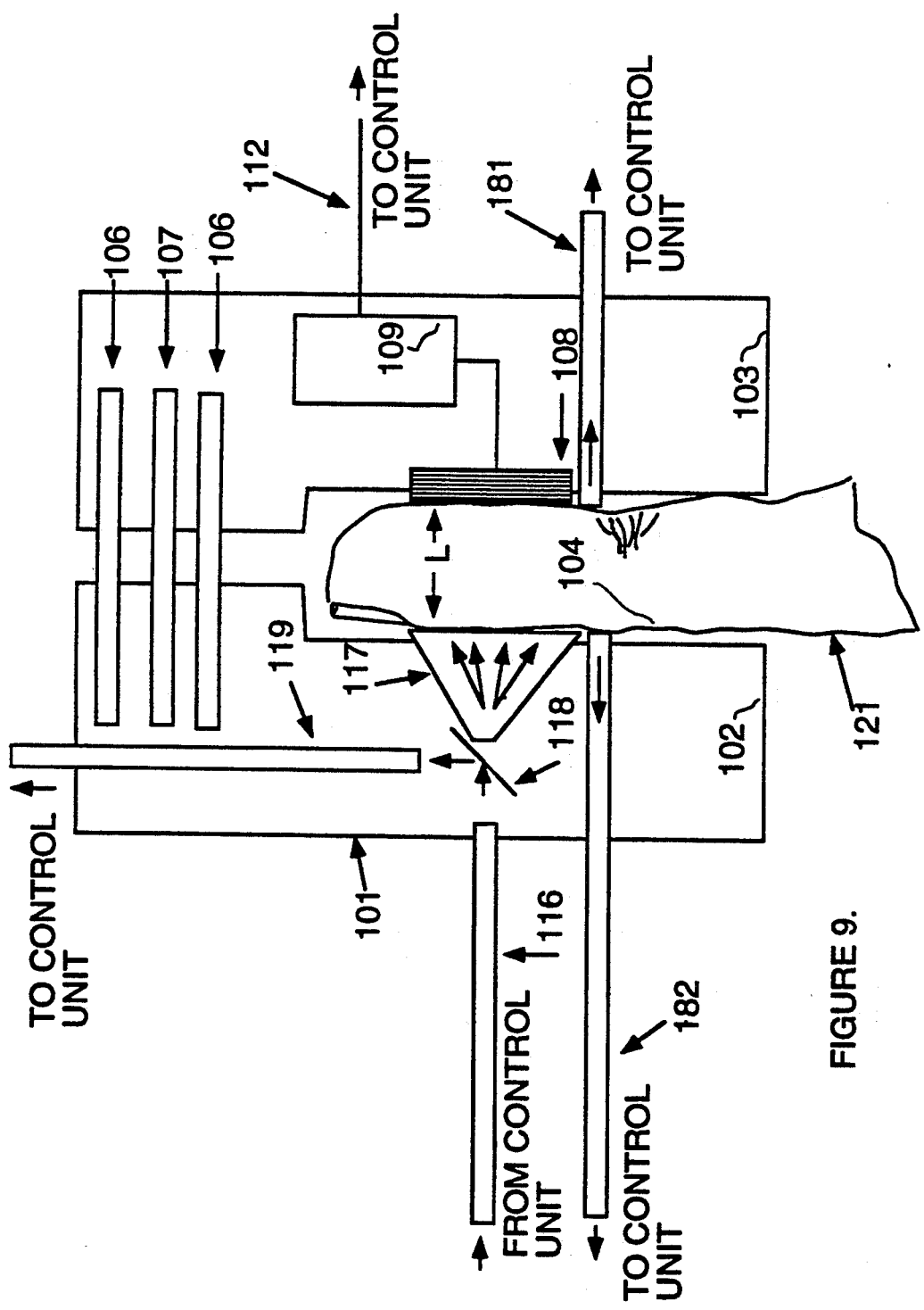
FIG. 9 is an illustration which shows a portion of the apparatus, particularly the clip assembly, associated with a second embodiment of the invention.
Figure 10:
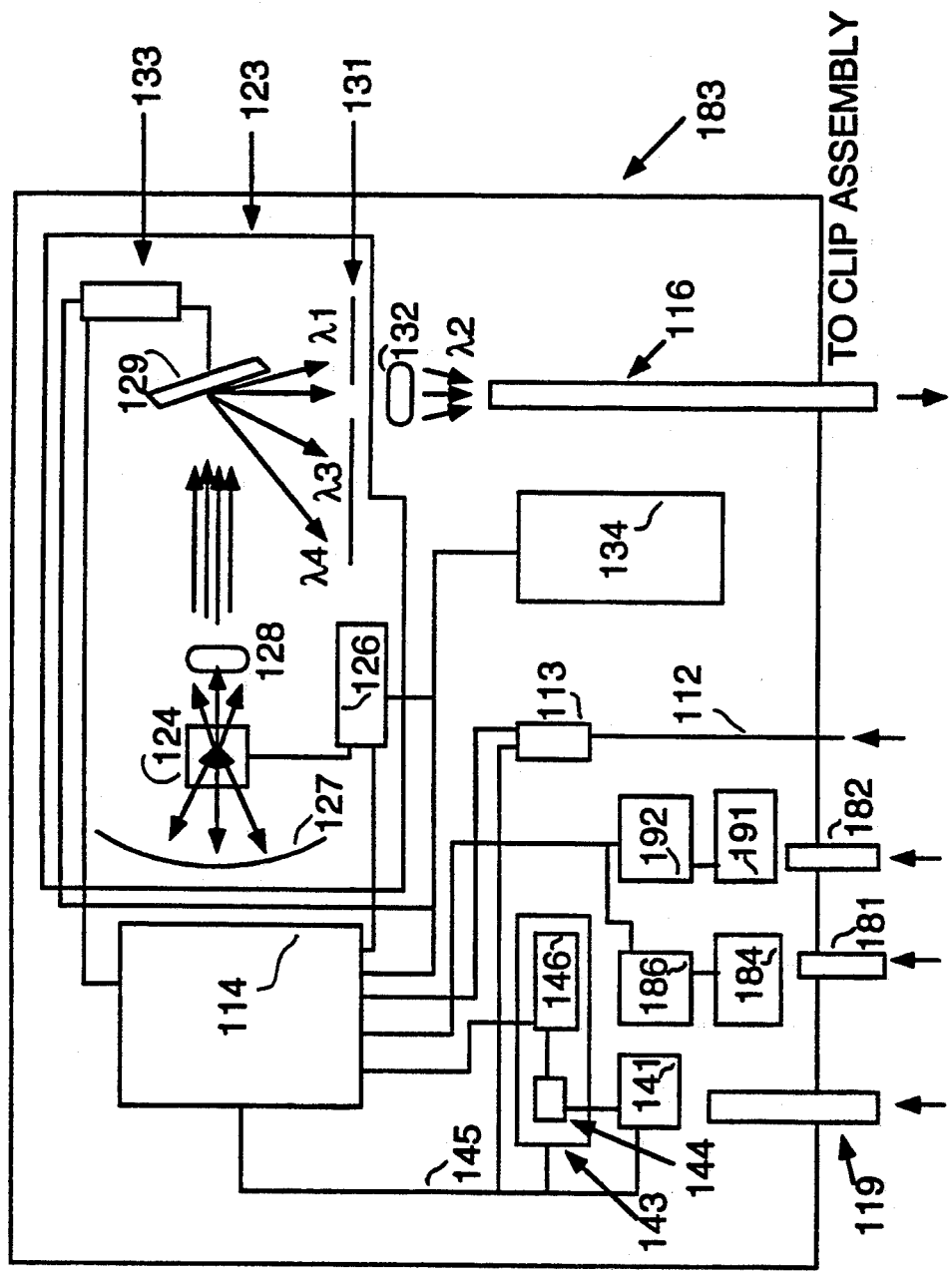
FIG. 10 is an illustration which shows a portion of the apparatus, particularly the control unit, associated with a second embodiment of the invention.

A second embodiment of this invention is illustrated in FIGS. 9 and 10; in FIG. 9 is shown an alternative embodiment of the clip assembly shown in FIG. 1. Elements having reference numerals have the same identities and the same description in FIG. 9 as in FIG. 1. The embodiment shown in FIG. 9 comprises several additional elements. Adjacent to the acoustic transducer 108 and positioned to collect light emitted from the tissue, is optical fiber means 181. A fourth optical fiber means 182 is so placed as to collect light reflected and scattered from near the surface of the tissue 104. Both of the optical fiber means 181, 182 are connected to the control unit 183 illustrated in FIG. 10 which is similar to control unit 111 of FIG. 2. Control unit 183 comprises several additional elements.

In FIG. 10, the elements having the same reference numbers as those in FIG. 2 have the same identities and descriptions. The light collected by optical fiber means 181, is transferred to the control unit 183 where it is detected by a detector assembly 184 and its intensity is measured. The electrical output from detector assembly 184 is processed by low noise electronic circuitry 186, which includes a low-noise amplifier, an integrator and a resettable peak-hold circuit. The signal is digitized and applied to the computer 114. The light collected by optical fiber means 182 is transferred to the control unit 183 where it is detected by a detector assembly 191 and its intensity is measured. The electrical output from detector assembly 192 is processed by low noise electronic circuitry 192, including a low-noise amplifier, an integrator and a resettable peak-hold circuit. The signal is digitized and applied to the computer 114.

The apparatus of the second embodiment differs from the apparatus of the first embodiment in that the intensity of the light transmitted through the tissue 104, and diffusely reflected from it, are monitored in addition to the intensity of the light incident on the tissue 104. The intensity of the generated acoustic signal is monitored and measured in both embodiments.

The operation of the second embodiment is analogous to the operation of the first embodiment except that the second embodiment provides for two additional measurements and the processing associated with them. The light transmitted through the tissue 104 is collected by fiber means 181, detected by detector 184 and recorded by the microcomputer 114 as $I_1(\lambda)$. Concurrently the light diffusely reflected from the tissue 104 is collected by optical fiber means 182, detected by detector 191 and recorded by computer 114 as $I_2(\lambda)$. These signals $I_1(\lambda)$, $I_2(\lambda)$ in addition to $I_0(\lambda)$, and $P(\lambda)$ can then be analyzed by a second method which is an enhancement to the first method.

The optical transmission, $Q(\lambda)$, of the tissue sample 104 at a wavelength, $\lambda$, may be described by the expression $$Q(\lambda) = I_1(\lambda)/I_0(\lambda) \tag{9}$$

In the geometry of embodiment 2, the optical transmission will be described by Eq. (2) in the case where scattering is the dominant attenuation mechanism in the medium (typically from 600 nm–1300 nm). In the case that absorption is the dominant attenuation mechanism in the medium (typically from 1900 to 2000 nm and at wavelengths longer than 2400 nm) the optical transmission will be described by Beer's law as represented in Eq. (6). In the indeterminate region where scattering and absorption are comparable no simple analytical expression adequately describes the optical transmission.

It is common in the field of NIR spectroscopy to define a function $$G(\lambda) = (\ln[1/Q(\lambda)])/L \qquad (10)$$

In the case where Beer's law is a valid descriptor of the radiation transport through the sample, $G = \mu_a$, but this will not be the case in general. The prior art, however, teaches how to use the algorithms and correlation techniques of chemometrics discussed earlier, together with a data set model, to deduce the concentrations of various components in the medium from the measured optical transmission function. As pointed out in the discussion of the prior art for this invention, this process is prone to error as a result of the strong and variable effects of scattering on the transport of radiation through the sample.

In the second embodiment of the invention the optical analysis described above is performed in parallel with the analysis of the acoustic signal, $P(\lambda)$ to determine the absorption coefficient, $\mu_a(\lambda)$. Correlations can then be made between $\mu_a(\lambda)$ and $G(\lambda)$ and both functions can be used as input data sets to the chemometric analysis techniques described earlier. As a result, the determination of component concentrations using this parallel measurement technique should exhibit increased accuracy and precision and be less subject to interference and outlier effects than when the acoustic measurement of embodiment 1 is used alone.

Additional information is obtained by recording the diffusely reflected light, $I_2(\lambda)$. The degree of diffusely reflected light is determined by the scattering and absorbing properties of the tissue sample. It is possible to make use of this information in conjunction with the analysis described above to further refine the analysis of component concentrations and sample composition.

The concentration of components may vary throughout the tissue. The analysis methods of embodiment two allow determination of component concentrations within the region of tissue bounded by the tissue surface and with a depth equal to one penetration depth, d, of the optical radiation. The optical techniques described in the prior art aim to measure the average concentration in the medium along the x axis. In certain instances it is desired to measure the concentration of the desired species at a particular depth, $x_1$, below the surface of the tissue.

Figure 6:
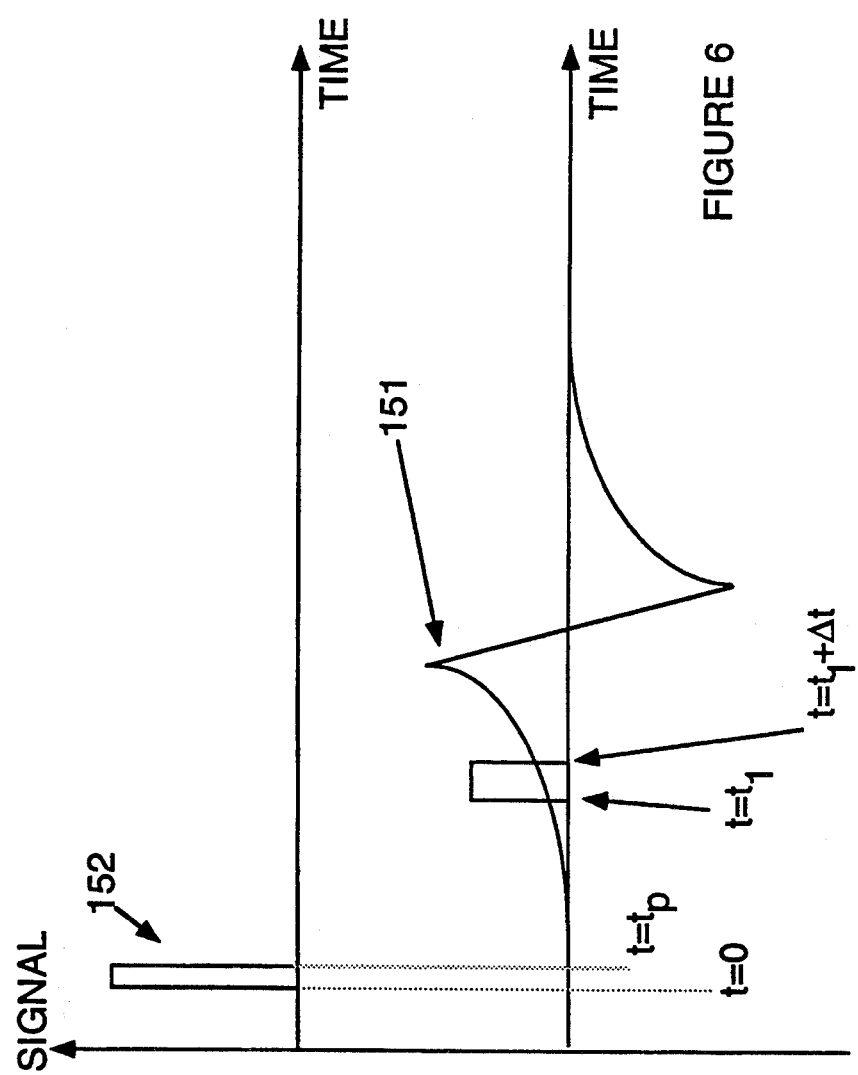
FIG. 6 is an enlarged view of a typical acoustic signal.

Consider a thin "slice" of tissue, of thickness $\Delta x$, lying in the plane normal to the x axis in FIG. 7 and extending from $x = x_1$ to $x = (x_1 + \Delta x)$. The acoustic signal from this slice will reach the acoustic detector after time $t_1 = (L - x_1 - \Delta x)/v$. By gating the output from the acoustic detector with a gate of width $\Delta t = \Delta x/v$ beginning at time $t_1$, the signal produced by absorption in the region of the desired "slice" is detected. This technique assumes that $t_p < \Delta t$ and that $t_p < t_1$ as well as that the response time of the acoustic detector is less than $\Delta t$. In general, the acoustic signal from the region of tissue where the beam enters the tissue reaches the detector later than, and is larger than, that measured by the above technique. The use of a gate allows the larger and later signal to be discarded. In FIG. 6 is illustrated the acoustic signal generated in the medium. Also shown is the gate of width $\Delta t$ by which the detected acoustic signal is gated. The measured acoustic signal is determined using Eq. (1).

In this case we can deduce I (0, $x_1$) from the measured optical intensities $I_0(\lambda)$, $I_1(\lambda)$ and $I_2(\lambda)$ and our knowledge of the radiation transport in the sample. All the variables in Eq. (1) except for $\mu_a$ are therefore known from optical and acoustic measurements or from calibration. Thus the material absorption coefficient can be deduced from the measured acoustic power in combination with the optical transmission and reflection measurements described with respect to the second embodiment, FIGS. 9 and 10.

While this embodiment has the advantage of allowing choice of the region of tissue to be studied, evaluation of Eq. (1) with representative values for the parameters shows that the detected acoustic signal will be reduced by an order of magnitude compared to the situation in embodiments one and two. This can be compensated for by using a more intense light source, or by using signal enhancement techniques.

Figure 11:
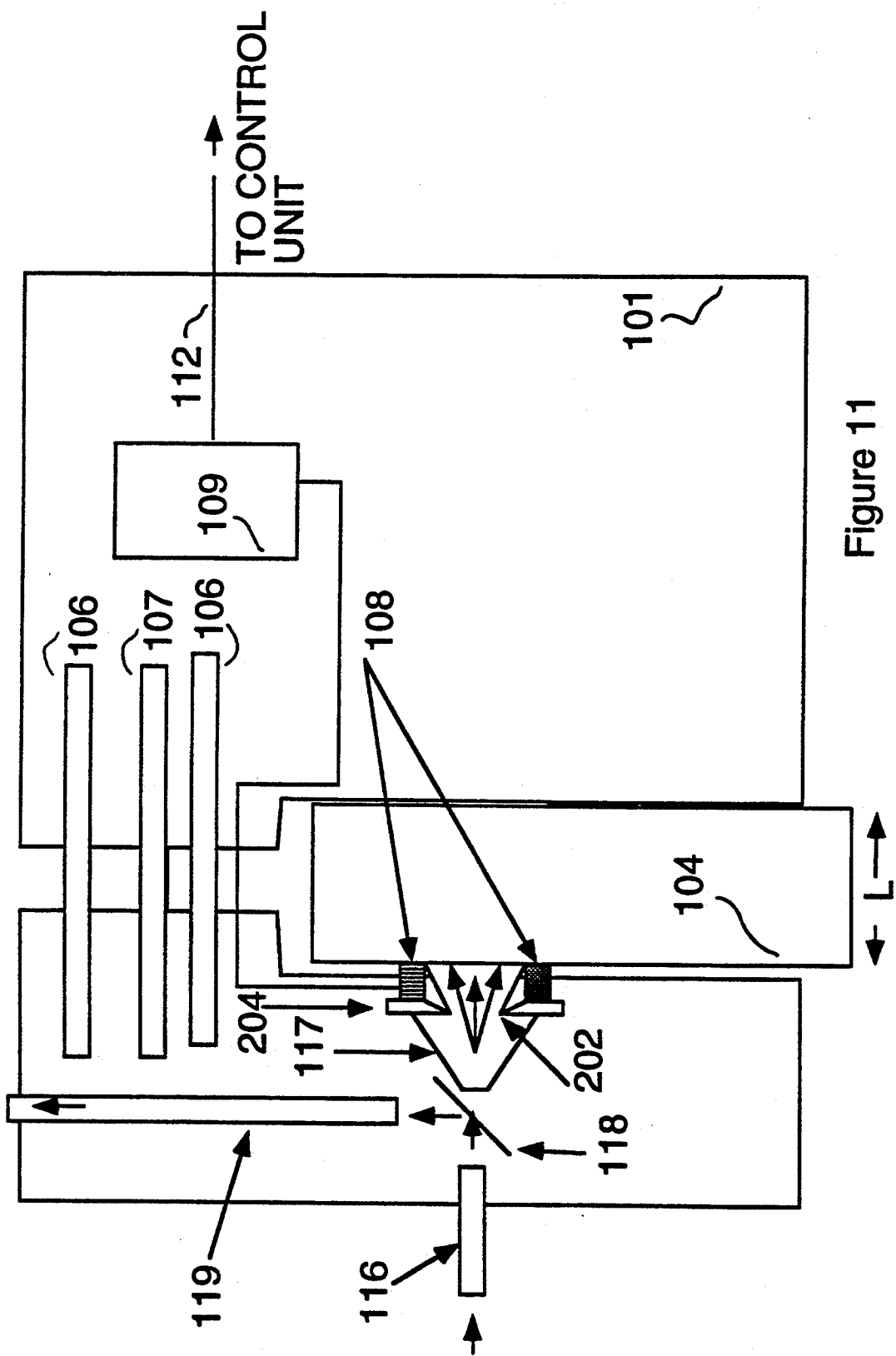
FIG. 11 is an illustration which shows a third embodiment of the apparatus according to the present invention.

A backward propagating acoustic signal can be employed in the analysis. Suitable apparatus is illustrated in FIG. 11. In this embodiment, the acoustic signal generated when light from optical fiber means 116, is absorbed in the tissue 104 is detected by acoustic transducer 108. This transducer 108 is manufactured in the form of an annulus through which the illuminating light may pass. Alternatively, the transducer may have the form of a disc placed adjacent to the beam expansion means 117. A shield 202 is built into the transducer mounting assembly 204 to prevent the incident beam 170 from impinging directly on the transducer 108. If the beam is permitted to impinge directly, it may generate a photo-acoustic signal in the transducer 108 not directly related to the tissue 104.

In general, when the acoustic wave is generated in the tissue it propagates both forward and backwards along the axis of propagation of the planar beam of radiation. The generated acoustic signal propagates forward to the far side of the tissue where it is detected as described above. In this embodiment the back-propagating acoustic signal is detected. Under some conditions of geometry and tissue properties this has advantages. One example where the detection of a backward propagating acoustic signal may be advantageously employed is the case where the tissue geometry precludes the placement of transducer 108, opposite the light source. It is apparent that the backward acoustic wave detection can be combined with slice detection and both combined with optical transmission and reflection as described above.

Figure 12:
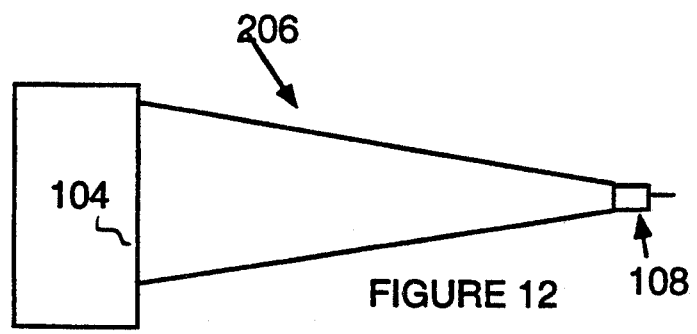
FIG. 12 is an illustration which shows a portion of the apparatus employing an acoustic concentrator.

The acoustic signal may be enhanced by placing a conical acoustic concentrator 206 between the transducer and the tissue as shown in FIG. 12. This concentrator 206 is made of a material, which is chosen to provide relatively high acoustic transmission, relatively low reflectance losses at the tissue interface, and an appropriate acoustic refractive index so as to allow concentration of the acoustic signal as it propagates from the tissue along the concentrator to the acoustic transducer 108, mounted at the end of the concentrator. A material such as Medicast 401 epoxy loaded with 50% aluminum oxide powder, for example, may be used.

The taper angle of the concentrator is chosen to provide minimum losses as the acoustic signal propagates along the concentrator. The outer surface of the concentrator is coated with a metallic material to provide high acoustic reflectivity. The acoustic signal at the transducer is enhanced by a factor of $(D_1/D_2)^2$ where $D_1$ is the diameter of the entrance and $D_2$ is the diamter at the transducer. Thus, if for example the concentrator has a diameter $D_1 = 1$ cm and $D_2 = 2$ mm, the signal is enhanced by a factor of 25.

Figure 13:
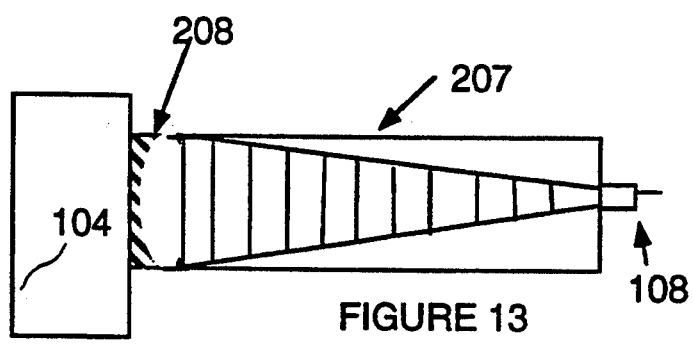
FIG. 13 is an illustration which shows a portion of the apparatus employing a cylindrical acoustic collector.

A cylindrical collector 207, FIG. 13, which has a converging acoustic refractive element such as a lens 208, at its input face may be used to concentrate the acoustic energy. The lens 208 and collector 207 are made of appropriate materials such as the loaded Medicast epoxy described previously. The acoustic amplification factor is $(D_1/D_4)^2$ where $D_4$ in this case is the diameter of the focused beam at the transducer, while $D_1$ is the diameter of the acoustic beam as it enters the acoustic lens 208. A minimum value of the focused acoustic beam diameter $D_4$ may be estimated from the standard diffraction relationship $D_4 \approx (f/D_1)w$, where $f$ is the focal length of the acoustic lens 208, and $w$ is the wavelength of the acoustic wave. For typical signals emanating from materials with geometries and material properties such as have been discussed earlier, a reasonable approximation is that $w \approx 2d \approx 2$ min. Selecting $D_1 = 1$ cm and $f = 2 D_1$, under these conditions the maximum acoustic enhancement factor would be approximately 6.

If the electromagnetic radiation is in the form of an optical pulse having a pulsewidth $t_p$, where $t_p$ is chosen to be longer than the acoustic transit time of one penetration depth, $t_a = d/v$. The acoustic signal will be a bipolar signal with a characteristic duration equal to $t_p$. In contrast, if $t_p$ is chosen so that $t_p < t_a$, then the acoustic signal will have a duration of $t_a$, which is a function of the tissue properties rather than solely of the apparatus. When the optical radiation incident on the tissue is pulsed at low frequency, the Fourier spectrum of the acoustic signal will be represented by a complex form function of roughly Gaussian shape with a center frequency of $f_1 = (2t_p)^{-1}$ and a half width of the same order of magnitude. If the tissue is repetitively pulsed with an optical signal at a frequency $f_2$ of the same order of magnitude as $f_1$, the acoustic signal will have a Fourier spectrum in the form of a series of narrow harmonics of $f_2$. In the case that $f_1 \approx f_2$, then only the harmonic at $f_2$ will have significant magnitude and the acoustic signal can be detected using narrow band filtering techniques, giving enhanced sensitivity.

For a typical tissue sample and measurement application such as has been described previously in this disclosure, the frequency $f_1$ is of the order of 1 MHz. An example would involve repetitive pulsing at 1 MHz of the light source while the grating, FIG. 2, is driven so as to present light at aperture 131 at the selected wavelength. The grating 129 would increment the wavelength at a frequency of between 10–100 kHz. In this way a series of 10–100 pulses would be incident on the tissue at each wavelength sequentially, while the generated acoustic signal would have a center frequency of 1 MHz and a moderately narrow bandwidth.

Figure 14:
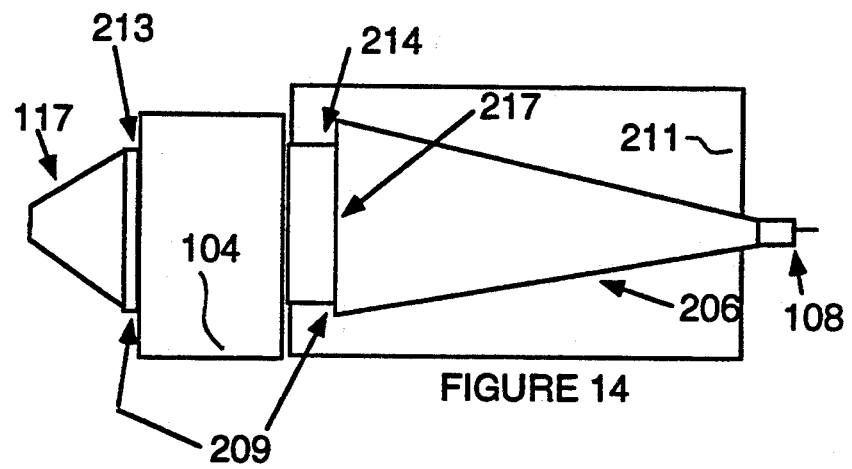
FIG. 14 is an illustration which shows a portion of the apparatus employing an acoustic resonator.

An acoustic resonator 209, FIG. 14, with a characteristic frequency that is a multiple of the frequency $f_2$ would provide increased sensitivity.

Separation between the acoustic transducer 108 and the beam expansion means 117 is substantially unchanged regardless of the thickness of the tissue sample under examination. The beam expansion means 117, is so designed as to include a plane surface made of a material such as fused silica, which is in contact with the tissue and through which the optical radiation is incident on the tissue. This silica surface 213 of beam expansion means 117 acts as a high reflectivity acoustic reflector and forms one mirror of the desired acoustic resonator 209. Opposite to the site of input of optical radiation to the tissue is the concentrator assembly 211. In this embodiment the medium of the conical concentrator 206 is chosen to have an acoustic impedance that results in a relatively high (ideally greater than 50%) reflectance for the acoustic signal at the interface between medium 214 and the acoustic concentrator 206. Medium 214 is chosen to be a material with an acoustic impedance substantially matched to that of tissue, and physical properties that enable it to maintain good contact between the tissue, 104, and the acoustic concentrator, 206, regardless of the thickness of the tissue sample. Such an acoustic coupling material 216 could be a liquid such as water contained in an envelope whereby gravity would cause the water to flow so as to fill the space between the tissue and concentrator 206. The entrance face 217 of the conical concentrator 206 is made to be substantially planar and oriented substantially parallel to the silica acoustic reflector 213 in the beam expansion means 117. The entrance face 217 of the concentrator 206 thus acts as the second acoustic reflector for the acoustic resonator 209 of this embodiment. The separation of the two reflectors, 213 and 217, is chosen to be a multiple of $f_2^{-1}$ so that the generated acoustic signal has a frequency that is a resonant mode of the acoustic resonator 209 cavity.

The use of such a resonant cavity detection scheme will result in enhanced sensitivity for detection of the generated acoustic signal over previously discussed embodiments. Such an approach is applicable both to the detection of acoustic signals from the initial penetration depth of the tissue as discussed in the first and second embodiments and to the detection of signals from particular depths in the tissue as described in the third embodiment.

The embodiment of the invention shown in FIG. 11 and described above can be used to measure the absolute value of the blood and tissue oxygenation in a human fetus in-utero.

Figure 15:
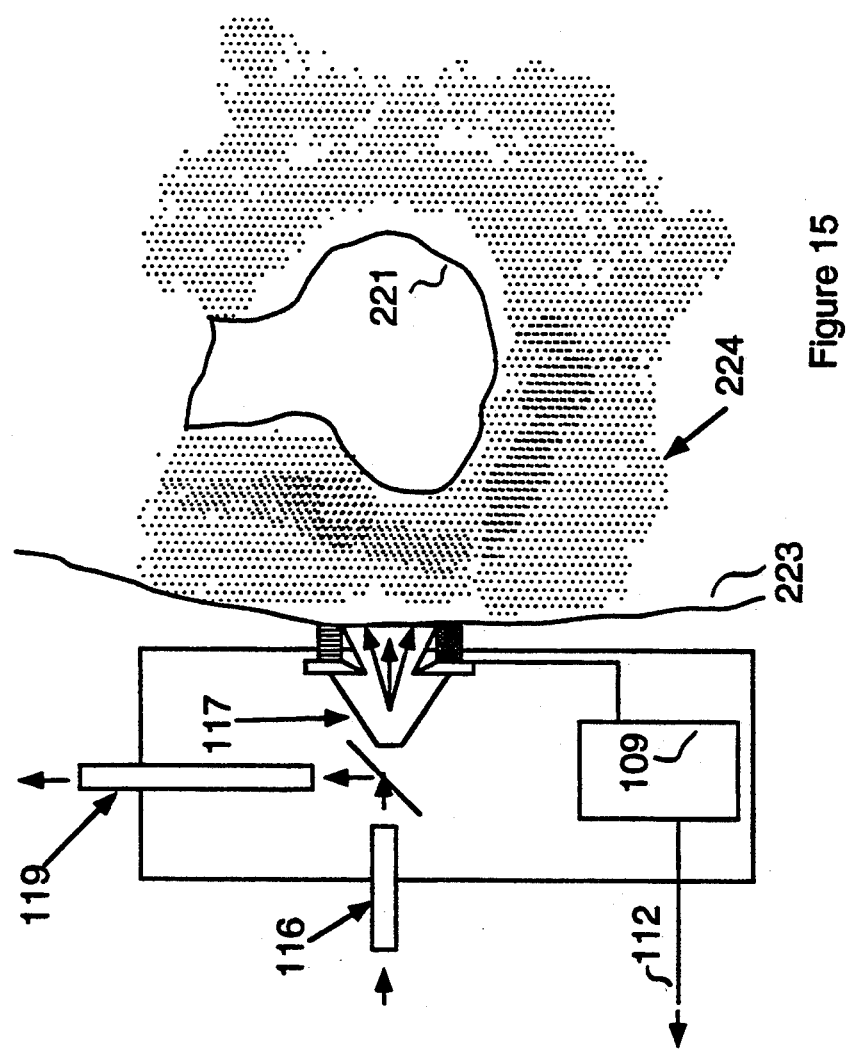
FIG. 15 is an illustration which shows a portion of the apparatus, particularly the probe assembly, associated with an embodiment of the invention adapted to measurements of a human fetus in-utero.

FIG. 15 shows an in-utero head 221 of a human fetus, external skin of the mother 223, and the subdermal tissues 224 between the mothers skin and the fetus 221 including but not limited to abdominal and uteral tissues, and amniotic fluid. The techniques of earlier embodiments are utilized to measure relative and absolute concentrations of chemical species within a human fetus in-utero. In particular this embodiment can be used to measure tissue oxygenation, blood saturation and possibly the concentrations of other blood chemicals in the fetus. In addition the concentrations of various components of the media surrounding the fetus can be measured.

It should be noted that the use of the time gating techniques of the third embodiment are particularly suited to this application since they allow measurement of oxygen concentration at a specifically selected site, such as in the brain of the fetus.

The apparatus and method of the present invention can be used to measure the concentration of chemical components in the human breast. Such measurements are believed to have the potential to provide early detection of breast cancer.

The apparatus can be used for performing in-vitro analysis of the sample under consideration to obtain the concentration of various components of the sample. The techniques of chemometrics and other advanced techniques for chemical analysis allow simultaneous determination of the concentration of multiple analytes in a single species. This analysis can be performed rapidly and economically using the techniques already described. Examples of applications of such an analysis would be for the in-vitro analysis of blood, urine or faeces samples.

The apparatus and method may be used to non-invasively analyze blood chemistry, and more particularly may be applied to non-invasive monitoring or measurement of blood glucose, blood cholesterol, bilirubin and other blood components and to monitoring the localized presence and concentration of systemic or topically applied therapeutic agents. The apparatus may be miniaturized for temporary or permanent implantation within a living organism, or use with endoscopic devices. In each of these internal applications, power and/or illumination may be applied from an external source via suitable electric cables, radiofrequency transmissions and fiber optics, and information may be provided to external processing equipment using similar cables, transmissions or optical fibers.

While the primary use of the methods and devices of this invention have been described with respect to human tissues or biological species, the invention is equally applicable to any biological system. It will therefore be applicable to veterinary medicine and animal research in general.

What is claimed:

1. The method of determining the concentration of a chemical species in condensed that scatters and absorbs electromagnetic energy comprising the steps of
    exciting a volume of said matter with electromagnetic energy of predetermined wavelength to cause said volume to generate acoustic energy,
    detecting said acoustic energy and generating a signal representative of the amplitude of the acoustic energy;
    developing a relationship between the amplitude of the acoustic energy generated in said condensed matter and the degree of absorption of said electromagnetic energy by said matter and chemical species; and
    analyzing the amplitude of said acoustic energy, making use of said relationship to determine the concentration of said species.

2. The method as in claim 1 in which the condensed matter is a biological material.

3. The method of determining the concentration of multiple or single chemical species in a sample which both scatters and absorbs electromagnetic energy comprising the steps of
    irradiating the sample with electromagnetic energy at selected wavelengths to cause the sample to generate acoustic energy;
    detecting the acoustic energy and generating signals representative of the amplitude of said acoustic energy at said wavelengths;
    developing a relationship between the amplitude of said acoustic energy in said sample and the degree of absorption by said sample and multiple or single species for each selected wavelength; and
    analyzing the dependence of the amplitude of said acoustic signal on the selected wavelength of the electromagnetic energy, making use of said relationship to determine the concentration of said multiple or single species in said sample.

4. The method of claim 3 including the additional steps of
    detecting the irradiating electromagnetic energy at said selected wavelengths after it has traversed a volume of said sample and generating intensity signals representative of the intensity of said electromagnetic radiation at said wavelengths;
    analyzing the dependence of said intensity signals on the selected wavelengths of the electromagnetic energy to determine the concentration of said multiple or single species; and
    correlating said electromagnetic and acoustic analysis to enhance the accuracy of said determination of concentration of said multiple or single species.

5. The method as in claims 1, 3 or 4 in which the scattering coefficient $\mu_s$ of the sample and the sample thickness L are selected such that $\mu_s L \gg 1$.

6. The method of claim 1, 3 or 4 in which the analysis is by multivariate analysis.

7. The method of claims 1, 3 or 4 in which the analysis is performed by comparison of the measured signals for the selected wavelengths with signals obtained from known or partially known mixtures of chemical species in said sample material.

8. The method as in claims 1, 3 or 4 in which the chemical species is glucose in blood.

9. The method as in claims 1, 3 or 4 in which the chemical species is oxygen in blood.

10. The method as in claims 3 or 4 in which the sample is biological material.

11. The method as in claims 1, 3, or 4 in which the analysis is made by partial least square correlation.

12. The method of determining the absorption coefficient of a biological substance comprising the steps of
    exciting a volume of said biological substance with electromagnetic energy of predetermined wavelength to cause said volume to generate acoustic energy within said medium whose amplitude is dependent upon the wavelength and intensity of said electromagnetic energy and the absorption coefficient of said biological substance at said wavelength;
    detecting said acoustic energy and generating a signal representative of the amplitude of said acoustic energy;
    developing a relationship between the amplitude of said acoustic energy in said biological substance and the degree of absorption of said electromagnetic energy, from said relationship and from the amplitude of the acoustic signal, determining the absorption coefficient of said biological substance at said wavelength.

13. The method of determining the concentration of a component species in an electromagnetic energy scattering medium comprising the steps of
    irradiating said medium with electromagnetic energy at selected wavelengths to cause said medium to generate acoustic energy within said medium whose amplitude is dependent upon the wavelength and intensity of said electromagnetic energy and the absorption coefficient of said component and scattering medium at said wavelength;
    scanning the wavelength of said electromagnetic energy over a predetermined range of frequencies;
    measuring the intensity of said electromagnetic energy at said wavelengths and generating an intensity signal representative of the intensity at each of said wavelengths;
    detecting the acoustic energy at said wavelengths to provide an output signal having an amplitude representative of the amplitude of said acoustic energy at said wavelengths; and determining the concentration of said component species by comparing the electromagnetic energy signal and the acoustic amplitude signal with known signals for component species in a scattering medium.

14. The method as in claim 13 in which the steps of irradiating, scanning, measuring and detecting are repeated a predetermined number of times and the electromagnetic energy intensity signals and the acoustic amplitude signals are stored and then averaged and the averaged signals are then used to determined the concentration of said species.

15. The method of determining the concentration of a component in a biological material, said method comprising the steps of exciting a volume of said material with electromagnetic energy to cause a finite volume of said material to generate acoustic energy whose amplitude is dependent upon the intensity and wavelength of said electromagnetic energy and the absorption coefficient of said component at said wavelength;

detecting said generated acoustic energy and generating a representative acoustic signal;

developing a relationship between the amplitude of said acoustic energy in said biological material and the degree of absorption of said electromagnetic energy by said biological material and said component;

determining by analysis from the intensity of the electromagnetic energy and the amplitude of the acoustic signal the absorption coefficient at said wavelength; and comparing said absorption at said wavelength with known absorption coefficients for various concentrations of said component to determine the concentration of said component.

16. The method of determining the concentration of a component chemical species in an electromagnetic energy scattering medium which comprises the steps of exciting a volume of said medium with electromagnetic energy at a predetermined wavelength to cause said medium to generate acoustic energy within said medium whose amplitude is dependent upon the wavelength and intensity of said electromagnetic energy and the absorption coefficient of said component species at said wavelength;

detecting said acoustic energy and generating a signal representative of the amplitude of the acoustic energy;

developing a relationship between the amplitude of said acoustic energy in said scattering medium and the degree of absorption of said electromagnetic energy by said medium and said chemical species;

determining from the intensity of said electromagnetic energy and the amplitude of the acoustic signal the absorption coefficient at said wavelength; and comparing said absorption coefficient at said wavelength with known absorption coefficients for said component at various concentrations to determine the concentration of said component.

17. The method of claim 16 which includes additionally the step of identifying the material composition which comprises the additional step of comparing said absorption coefficient at said wavelength with known absorption coefficients of various components or various concentrations to determine not only the concentration of said component but also to identify the components.

18. The method as in claim 12, 13, 14, 15, or 16 in which the acoustic energy is gated to detect acoustic signals generated at a selected volume.

19. The method as in claims 14 or 16 wherein the component is oxygen.

20. The method of determining the concentration of chemical species in an electromagnetic energy scattering medium which comprises the steps of irradiating said material with electromagnetic energy to cause said medium to generate acoustic energy within said medium whose amplitude is dependent upon the wavelength and intensity of said electromagnetic energy and the absorption coefficient of aid species at said wavelength;

scanning the wavelength of said electromagnetic energy over a predetermined band of wavelengths;

measuring the intensity of said electromagnetic energy at said scanned wavelengths and generating an intensity signal representative of the intensity at each of said scanned wavelengths;

detecting the acoustic energy at said wavelengths to provide an output signal having an amplitude representative of said acoustic energy at said wavelengths;

developing a relationship between the amplitude of said acoustic energy in said medium and the degree of absorption in said medium for each of said scanned wavelengths;

determining from the electromagnetic energy signal and the acoustic energy signal the absorption coefficient of said species and scattering medium at said wavelengths; and comparing said absorption coefficients at said wavelengths with known absorption coefficients for various concentrations of said species to determine the concentrations of said species.

21. The method as in claim 20 which includes additionally the step of identifying the material composition which comprises the additional step of comparing said absorption coefficients at said scanned wavelengths with known absorption coefficients of various components or various concentrations to determine not only the concentration of said components but also to identify the components.

22. The method as in claims 13, 14, 15, 16, 20 or 17 in which the component is within biological tissue.

23. The method as in claim 13, 14, 15, 16, 20, or 17 in which the component is in vitro material.

24. The method as in claims 12, 13, 14, 15, 16, 20 or 17 including the additional step of detecting electromagnetic energy which is transmitted through the material to generate a transmitted radiation signal and comparing the intensity of the transmitted signal to the intensity of the irradiation signal to determine an optical absorption coefficient.

25. The method as in claims 13, 16 or 17 wherein the component is blood glucose.

26. The apparatus for determining the concentration of species in a biological substance comprising electromechanical means for exciting a volume of said material with electromagnetic energy to cause a finite volume of said material to generate acoustic energy whose amplitude is dependent upon the intensity and wavelength of said electromagnetic energy and the absorption coefficient of said species;

transducer means for detecting said generated acoustic energy and generating a representative acoustic signal;

processing means for developing a relationship between the amplitude of said acoustic energy in said biological substance and the degree of absorption of said electromagnetic energy by said biological substance; and processing means for receiving said acoustic signal, making use of the relationship and determining the concentration of said species.

27. Apparatus for determining the concentration of a component in an electromagnetic energy scattering medium which comprises means for irradiating said material with electromagnetic energy at selected wavelengths to cause said medium to generate acoustic energy within said medium whose amplitude is dependent upon the wavelength and intensity of said electromagnetic energy and the absorption coefficient of said component and scattering medium at said wavelength;

means for scanning the selected wavelengths of said electromagnetic energy over a predetermined band;

means for detecting the acoustic energy at said wavelengths and providing an output signal having an amplitude representative of said acoustic energy at said wavelengths;

means for determining from the acoustic amplitude signal and the intensity of said electromagnetic energy the absorption coefficient of said component and scattering medium at said wavelengths; and means for comparing said absorption coefficients at said wavelengths with known absorption coefficients for various concentrations of said components to determine the concentration of said components.

28. The apparatus as in claim 26 or 27 in which means are provided for storing the acoustic amplitude signals and averaging said signals over a plurality of scans before determining the concentration.

29. The apparatus as in claim 26 or 27 including gating means to gate the acoustic signal to detect acoustic signals generated at a selected volume within the sample.

30. The apparatus as in claim 27 in which the component is within biological tissue.

31. The apparatus as in claim 27 in which the component is in in-vitro material.

* * * * *

UNITED STATES PATENT AND TRADEMARK OFFICE
CERTIFICATE OF CORRECTION

PATENT NO. : 5,348,002
DATED : September 20, 1994
INVENTOR(S) : Richard G. Caro

It is certified that error appears in the above-indentified patent and that said Letters Patent is hereby corrected as shown below:

Column 23, line 29, after "condensed" insert --matter--
Column 24, line 14, change "$\mu$" to --$\mu_s$--
Column 26, line 17, change "aid" to --said--

Signed and Sealed this

Eighteenth Day of May, 1999

Q. TODD DICKINSON

*Attest:*

*Attesting Officer*    Acting Commissioner of Patents and Trademarks